(12) United States Patent
Tamura et al.

(10) Patent No.: US 9,775,225 B2
(45) Date of Patent: Sep. 26, 2017

(54) X-RAY COMPUTED TOMOGRAPHY APPARATUS AND PHOTON COUNTING CT APPARATUS

(71) Applicant: Toshiba Medical Systems Corporation, Otawara-shi (JP)

(72) Inventors: Emi Tamura, Nasushiobara (JP); Yasuo Saito, Nasushiobara (JP); Takuzo Takayama, Utsunomiya (JP); Hiroaki Miyazaki, Otawara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 197 days.

(21) Appl. No.: 14/741,518

(22) Filed: Jun. 17, 2015

(65) Prior Publication Data
US 2015/0312998 A1    Oct. 29, 2015

Related U.S. Application Data

(63) Continuation of application No. PCT/JP2015/050148, filed on Jan. 6, 2015.

(30) Foreign Application Priority Data

Jan. 6, 2014   (JP) .................. 2014-000595

(51) Int. Cl.
*A61B 6/00* (2006.01)
*H05G 1/32* (2006.01)
(Continued)

(52) U.S. Cl.
CPC .............. *H05G 1/32* (2013.01); *A61B 6/032* (2013.01); *A61B 6/06* (2013.01); *A61B 6/4007* (2013.01);
(Continued)

(58) Field of Classification Search
CPC ..... A61B 6/032; A61B 6/4014; A61B 6/4007; A61B 6/035
See application file for complete search history.

(56) References Cited

U.S. PATENT DOCUMENTS

| | | | | |
|---|---|---|---|---|
| 6,333,968 | B1* | 12/2001 | Whitlock | B82Y 10/00 378/122 |
| 2005/0111610 | A1* | 5/2005 | De Man | A61B 6/032 378/10 |
| 2009/0034678 | A1* | 2/2009 | Popescu | A61B 6/032 378/10 |

FOREIGN PATENT DOCUMENTS

| | | |
|---|---|---|
| JP | 2005-110722 A | 4/2005 |
| JP | 2007-267980 A | 10/2007 |
| JP | 2005-177469 A | 7/2008 |

OTHER PUBLICATIONS

International Search Report issued Mar. 24, 2015 for PCT/JP2015/050148 filed on Jan. 6, 2015 with English Translation of Categories.

(Continued)

*Primary Examiner* — Hoon Song
(74) *Attorney, Agent, or Firm* — Oblon, McClelland, Maier & Neustadt, L.L.P.

(57) ABSTRACT

A gantry includes two X-ray source rings and a detector ring. Each X-ray source ring includes a plurality of X-ray sources arrayed circumferentially. The detector ring is provided next to the X-ray source ring and includes a plurality of X-ray detectors arrayed circumferentially. Each of the plurality of X-ray detectors detects X-rays from the X-ray source ring. A data collection circuit collects raw data corresponding to the intensity of the detected X-rays. A reconstruction unit reconstructs the collected raw data into a CT image based on digital data.

6 Claims, 17 Drawing Sheets

(51) Int. Cl.
*A61B 6/03* (2006.01)
*A61B 6/06* (2006.01)
*H01J 35/06* (2006.01)
*H01J 35/04* (2006.01)

(52) U.S. Cl.
CPC .......... *A61B 6/4035* (2013.01); *A61B 6/4266* (2013.01); *A61B 6/44* (2013.01); *A61B 6/482* (2013.01); *A61B 6/5205* (2013.01); *A61B 6/54* (2013.01); *A61B 6/56* (2013.01); *H01J 35/065* (2013.01); *A61B 6/035* (2013.01); *A61B 6/4241* (2013.01); *A61B 6/4488* (2013.01); *A61B 6/503* (2013.01); *H01J 35/045* (2013.01); *H01J 2235/062* (2013.01); *H01J 2235/068* (2013.01)

(56) References Cited

OTHER PUBLICATIONS

Written Opinion issued Mar. 24, 2015 for PCT/JP2015/050148 filed on Jan. 6, 2015.
English version of International Search Report issued Mar. 24, 2015 in PCT/JP2015/050148 (original version previously filed Jun. 17, 2015).

* cited by examiner

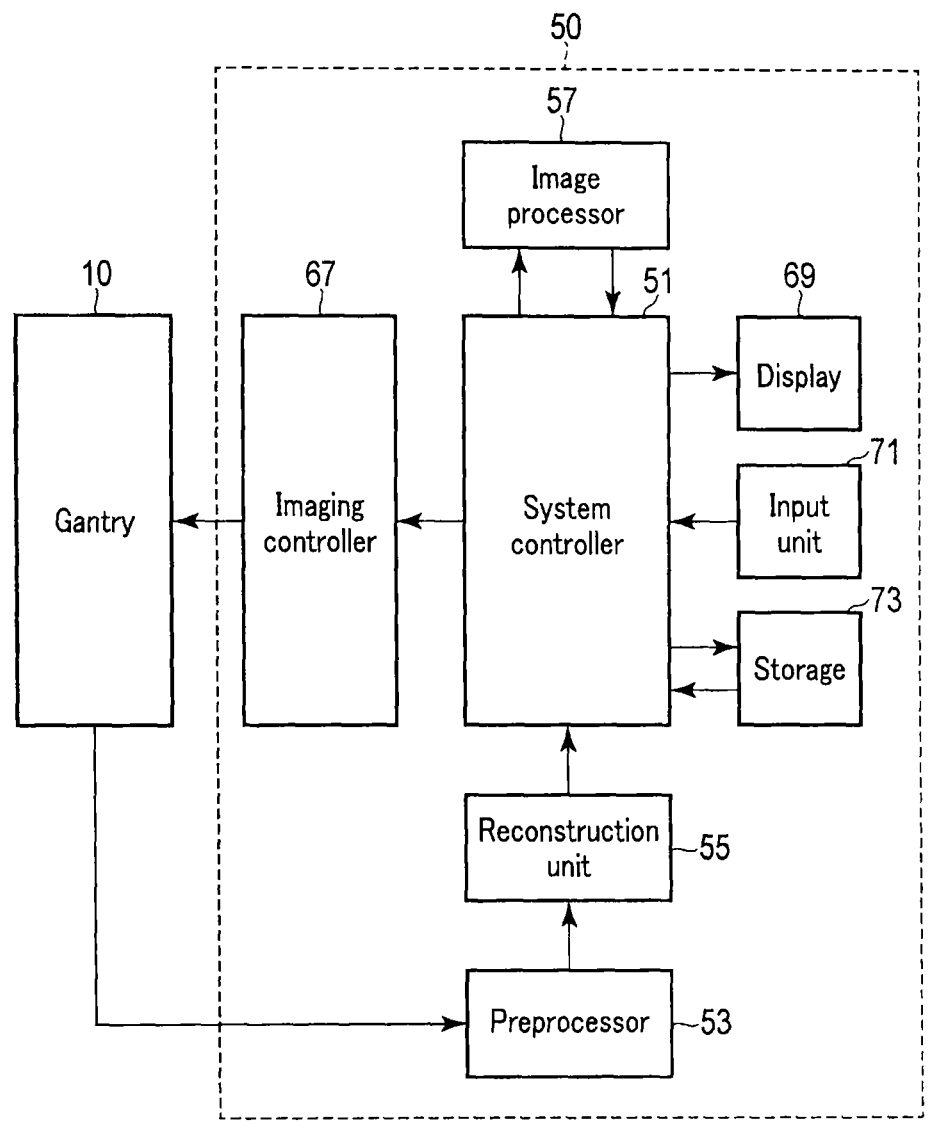
F I G. 1

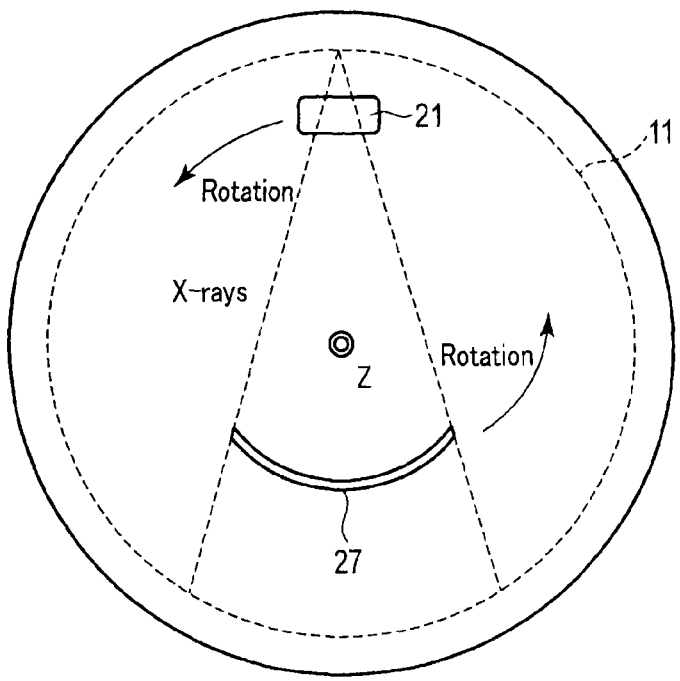
F I G. 10A
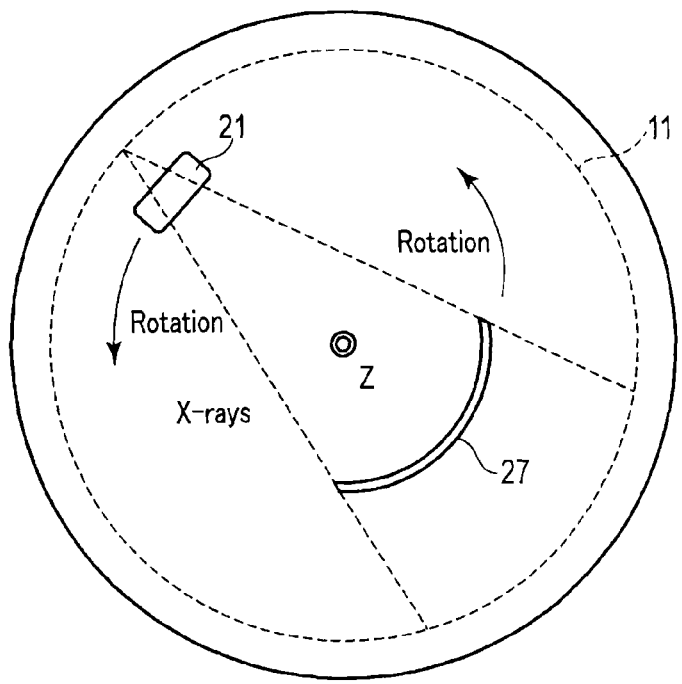
F I G. 10B

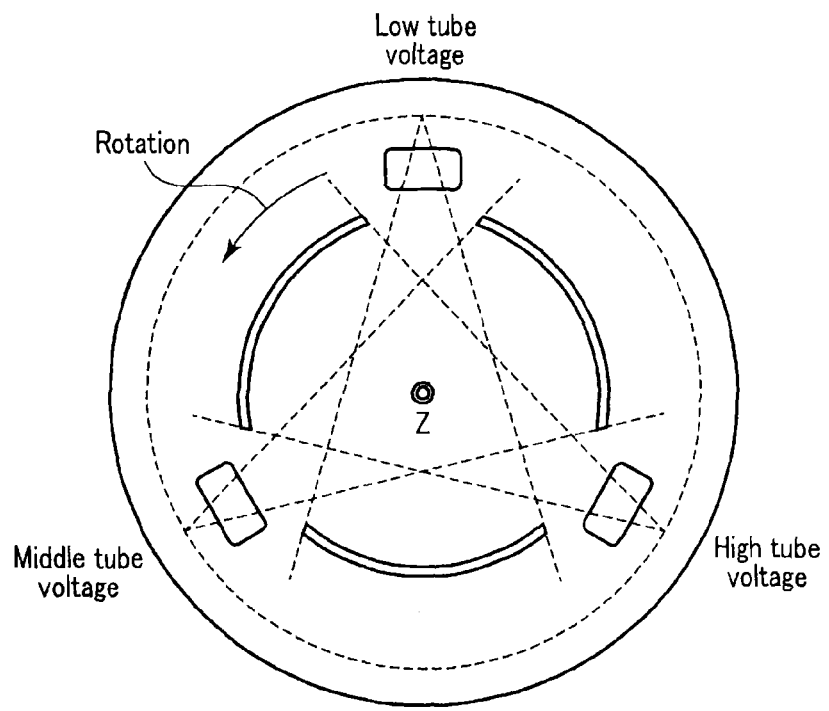
F I G. 15A
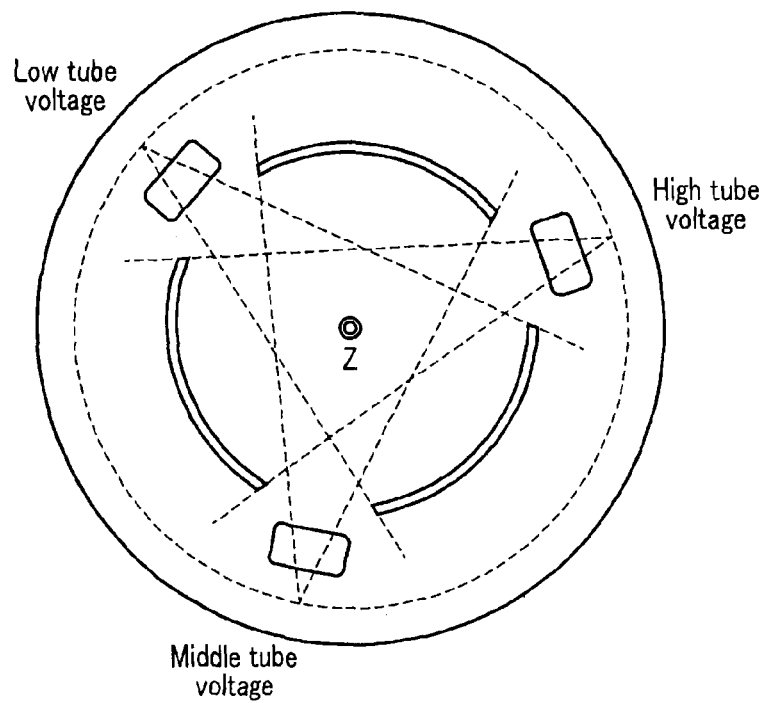
F I G. 15B

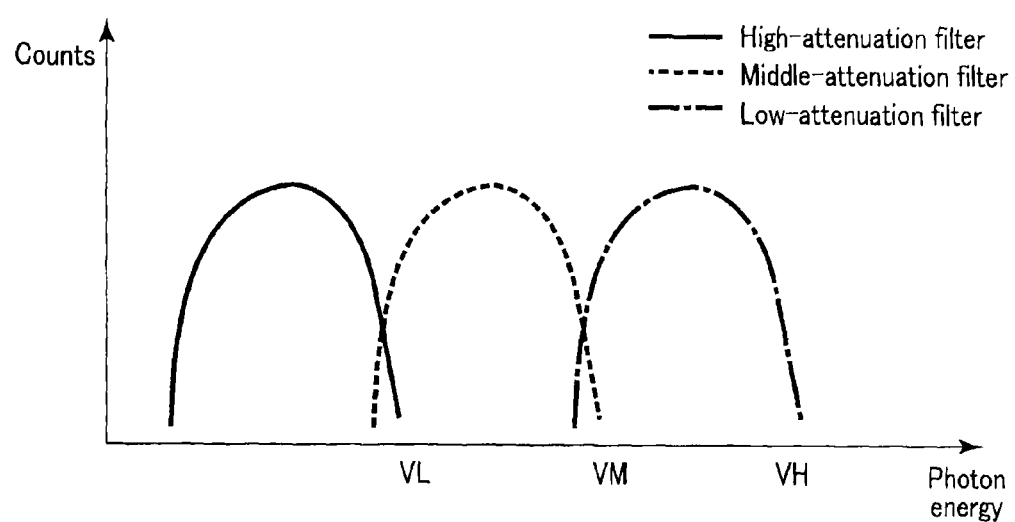
F I G. 16

X-RAY COMPUTED TOMOGRAPHY APPARATUS AND PHOTON COUNTING CT APPARATUS

CROSS-REFERENCE TO RELATED APPLICATIONS

This application is a Continuation Application of PCT Application No. PCT/JP2015/050148, filed Jan. 6, 2015 and based upon and claims the benefit of priority from the Japanese Patent Application No. 2014-000595, filed Jan. 6, 2014, the entire contents of which are incorporated herein by reference.

FIELD

Embodiments described herein relate generally to an X-ray computed tomography apparatus and a photon counting CT apparatus.

BACKGROUND

In third-generation CT, raw data is collected by rotating a rotating ring equipped with one or more sets of X-ray tubes and X-ray detectors. The rotating ring has reached the highest rotational speed of 0.275 s/rot. In physics, the centrifugal force generated by rotation is proportional to the square of angular velocity. For this reason, it is difficult to greatly increase the current rotational speed of the rotating ring. In fifth-generation CT, an electron gun is used to emit an electron beam from the rear side of a gantry, and the electron path is deflected by using a coil to cause the electron beam to strike anodes arrayed on a circumference, thereby generating X-rays. An electron beam is deflected onto the circumference to implement CT. In fifth-generation CT, since X-ray detectors are arrayed on a circumference, the scan time is determined by the electron beam scan time. The scan time according to the fifth-generation CT has reached 50 ms to 100 ms.

U.S. Pat. No. 7,634,045 has proposed a scheme of rotating only the detector side collimator (post-collimator) mounted on a gantry in fifth-generation CT. U.S. Pat. No. 7,634,045 has also presented fifth-generation CT which can also cope with spectral CT by changing an applied voltage for each place. This scheme, however, uses an electron gun, and hence the overall size of the system becomes large. In addition, since an X-ray detector and an electron beam are offset from each other in terms of a positional relationship, this scheme is not suitable for three-dimensional scanning (volume scanning).

BRIEF DESCRIPTION OF THE DRAWING

FIG. 1 is a functional block diagram of an X-ray computed tomography apparatus according to the first embodiment.

FIG. 10A is a plan view showing the placement of an X-ray source, a wedge filter, and a post-collimator at time t when the number of X-ray sources simultaneously driven is one according to the first embodiment.

FIG. 10B is a plan view showing the placement of the X-ray source, the wedge filter, and the post-collimator at time t+Δt when the number of X-ray sources simultaneously driven is one according to the first embodiment.

FIG. 15A is a plan view showing the placement of the X-ray sources, the wedge filters, and the post-collimators at time t when the number of X-ray sources simultaneously driven is three in tube-voltage-based spectral CT according to the application example of the first embodiment.

FIG. 15B is a plan view showing the placement of the X-ray sources, the wedge filters, and the post-collimators at time t+Δt when the number of X-ray sources simultaneously driven is three in tube-voltage-based spectral CT according to the application example of the first embodiment.

FIG. 16 is a graph schematically showing the energy spectra of X-rays emitted from an X-ray source and transmitted through wedge filters with different X-ray attenuation coefficients according to the application example of the first embodiment.

DETAILED DESCRIPTION

In general, according to one embodiment, an X-ray computed tomography apparatus includes two X-ray source rings, a single detector ring, a data collection unit, and a reconstruction unit. The two X-ray source rings are arrayed along a central axis. Each of the two X-ray source rings includes a plurality of X-ray sources arrayed on a circumference. The single detector ring is provided between the two X-ray source rings and including a plurality of X-ray detectors arrayed on a circumference. Each of the plurality of X-ray detectors detecting X-rays from the two X-ray source rings. The data collection unit is configured to collect digital data corresponding to an intensity of the detected X-rays. The reconstruction unit is configured to reconstruct a CT image based on the digital data.

An X-ray computed tomography apparatus and a photon counting CT apparatus according to an embodiment will be described below with reference to the accompanying drawings.

First Embodiment

FIG. 1 is a functional block diagram of an X-ray computed tomography apparatus according to the first embodiment. As shown in FIG. 1, the X-ray computed tomography apparatus according to the first embodiment includes a gantry 10 and a console 50. The gantry 10 is installed in, for example, a CT imaging room. The console 50 is installed, for example, in an imaging control room adjacent to the CT imaging room. The gantry 10 and the console 50 are communicably connected to each other via a network or the like.

Figure 2:
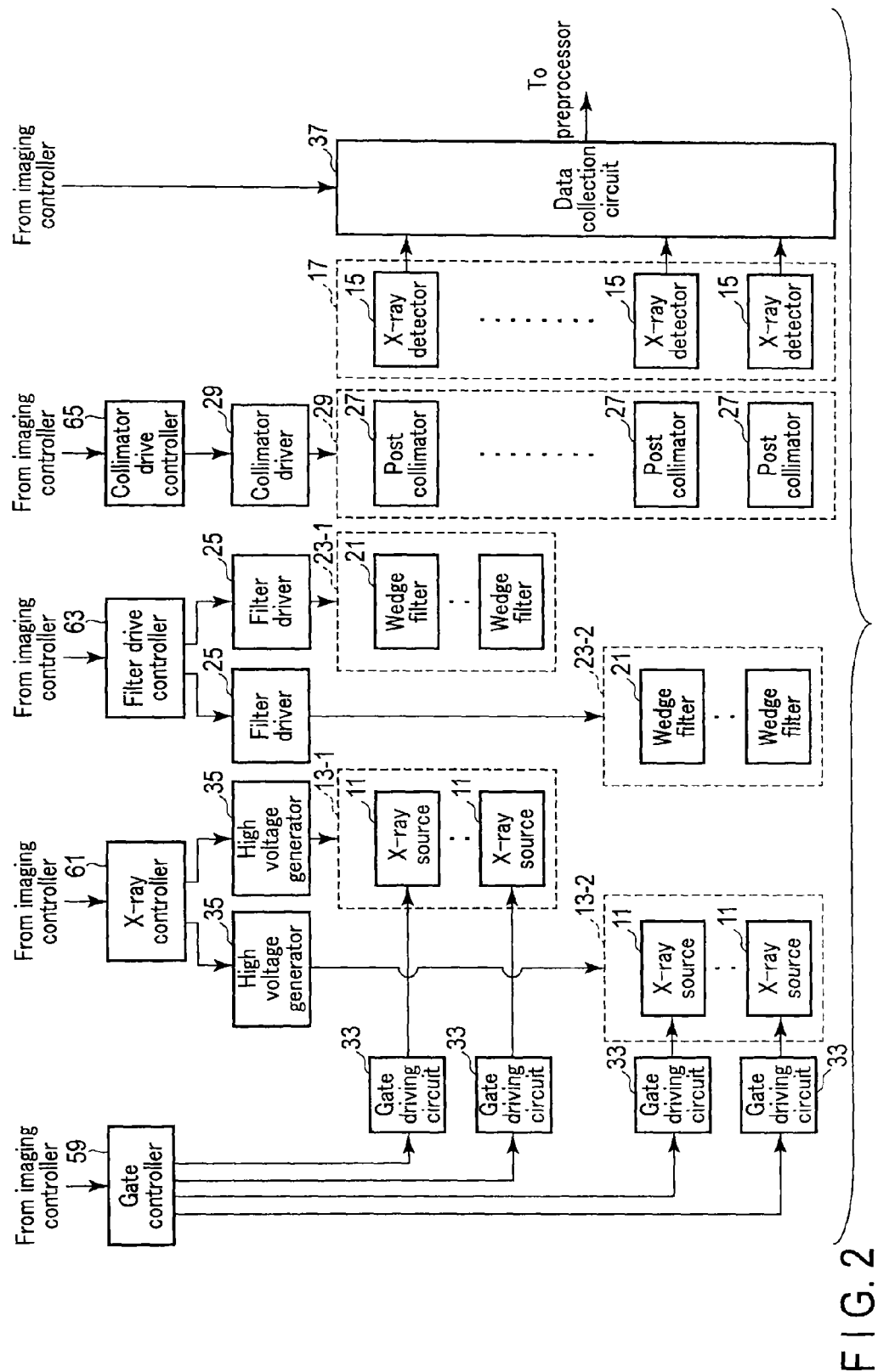
FIG. 2 is a functional block diagram of a gantry in FIG. 1.
Figure 3:
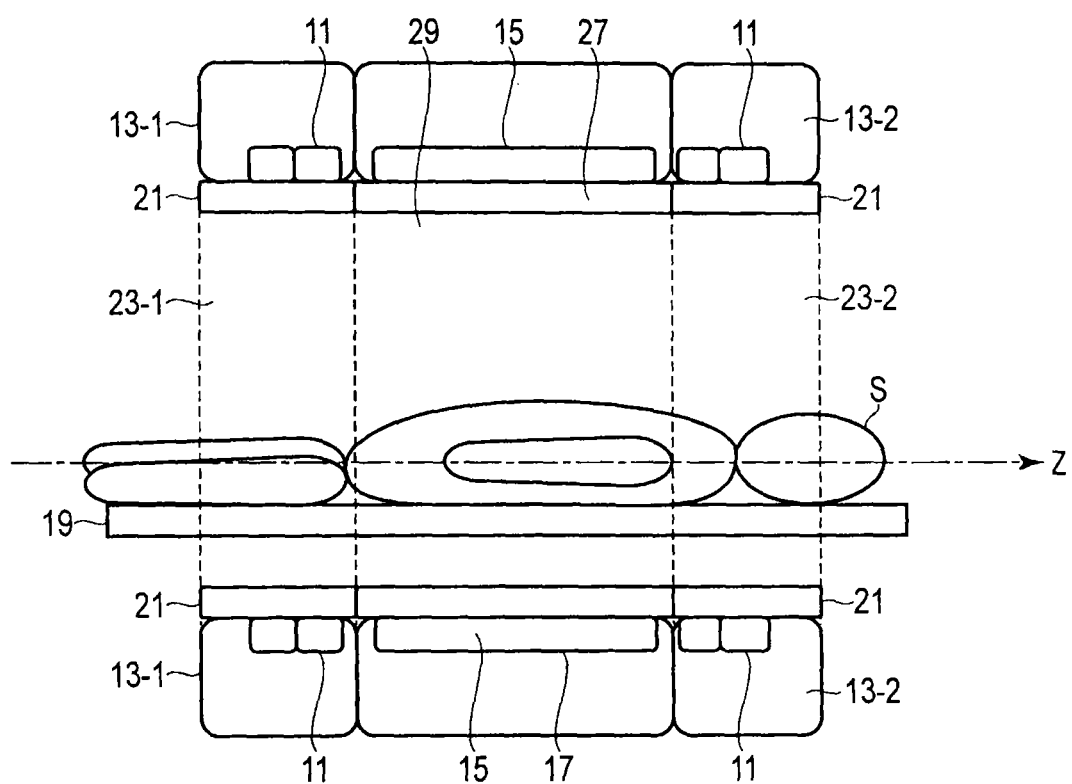
FIG. 3 is a view schematically showing the structure of a gantry in FIG. 2.

FIG. 2 is a functional block diagram of the gantry 10. FIG. 3 is a view schematically showing the structure of the gantry 10. As shown in FIGS. 2 and 3, the gantry 10 includes two annular structures (to be referred to as X-ray source rings hereinafter) 13 accommodating a plurality of X-ray sources 11 and a single annular structure (to be referred to as a detector ring hereinafter) 17 accommodating a plurality of X-ray detectors 15. The detector ring 17 is arranged between an X-ray source ring 13-1 and an X-ray source ring 13-2. More specifically, the X-ray source ring 13-1, the X-ray source ring 13-2, and the detector ring 17 are arrayed along a central axis Z such that the their central axes spatially coincide with each other. The X-ray source ring 13-1, the X-ray source ring 13-2, and the detector ring 17 share an opening. The interior of the opening is set as an FOV (field of view). A top 19 supported on a bed (not show) is inserted into the opening. The subject S is placed on the top 19. The top 19 is positioned such that an imaging region of the subject S is included in the FOV. Note that in the following description, the two X-ray source ring 13-1 and the X-ray source ring 13-2 will be collectively called the X-ray source ring 13 when they are not discriminated from each other.

Figure 4:
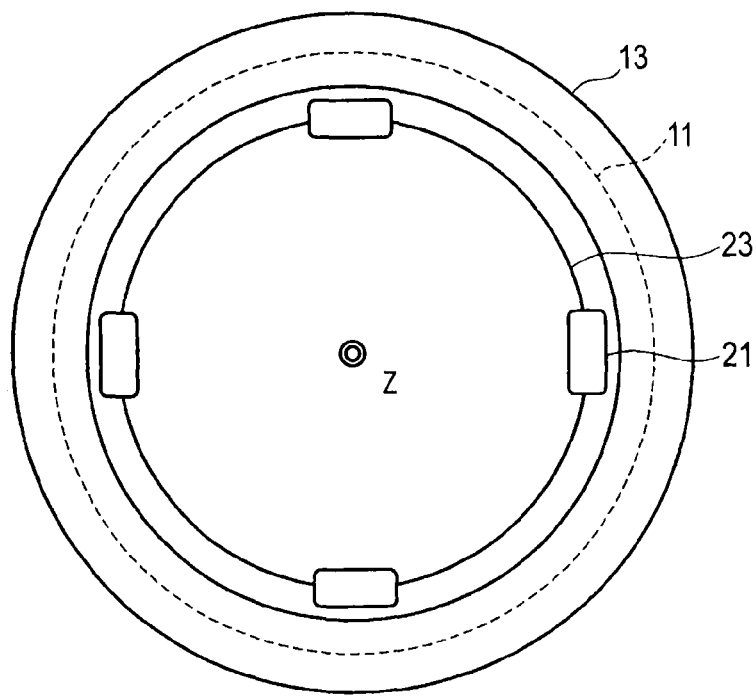
FIG. 4 is a schematic sectional view of an X-ray source ring in FIG. 2.

FIG. 4 is a schematic sectional view of the X-ray source ring 13. Note that the X-ray source ring 13-1 has almost the same structure as the X-ray source ring 13-2. As shown in FIG. 4, the X-ray source ring 13 includes the plurality of X-ray sources 11 arrayed circumferentially. In addition, the plurality of X-ray sources 11 may be arrayed along the rotation axis Z. Arraying the plurality of X-ray sources 11 along the rotation axis Z can irradiate a three-dimensional spatial region with X-rays. This makes it possible to perform volume scanning.

Each of the plurality of X-ray sources 11 generates X-rays. As the X-ray sources 11, cold cathode X-ray tubes are used. A vacuum is maintained in the interior of the X-ray source ring 13. That is, the X-ray source ring 13 functions as a vacuum vessel. This makes all the X-ray sources 11 be arranged in a vacuum. A plurality of wedge filters 21 are arranged outside the X-ray source ring 13 on its inner circumferential side. The plurality of wedge filters 21 are supported by, for example, an annular support member (to be referred to as a filter support member hereinafter) 23 so as to be rotatable about the central axis Z. The filter support member 23 is provided for each X-ray source ring 13. More specifically, a filter support member 23-1 is provided for the X-ray source ring 13-1, and a filter support member 23-2 is provided for the X-ray source ring 13-2.

Each wedge filter 21 is an X-ray attenuation filter for spatially unifying the dose of X-rays applied from each X-ray source 11 to the subject S. The number of wedge filters 21 to be installed is not specifically limited as long as it is one or more. More specifically, the number of wedge filters 21 to be installed is equal to the number of directions in which X-ray irradiation is simultaneously performed from the X-ray source 11. In the case shown in FIG. 4, the number of wedge filters 21 installed is four. The filter support member 23-1 is connected to a filter driver 25-1. The filter support member 23-2 is connected to a filter driver 25-2. Note that the number of directions in which X-ray irradiation is simultaneously performed set for the X-ray source ring 13-1 is equal to that for the X-ray source ring 13-2. In the following description, the two filter support members 23-1 and 23-2 are collectively called filter support members 23 when they are not discriminated from each other, and the two filter drivers 25-1 and 25-2 are collectively called filter drivers 25 when they are not discriminated from each other.

The filter driver 25-1 and the filter driver 25-2 are connected to a filter drive controller 63. The filter driver 25-1 and the filter driver 25-2 each generate motive power under the control of the filter drive controller 63. Upon receiving the motive power, the filter support member 23 rotates about the central axis Z at a predetermined angular velocity. The filter support member 23 rotates independently of the X-ray source ring 13. That is, even when the filter support member 23 rotates, the X-ray source ring 13 remains stationary.

Figure 5:
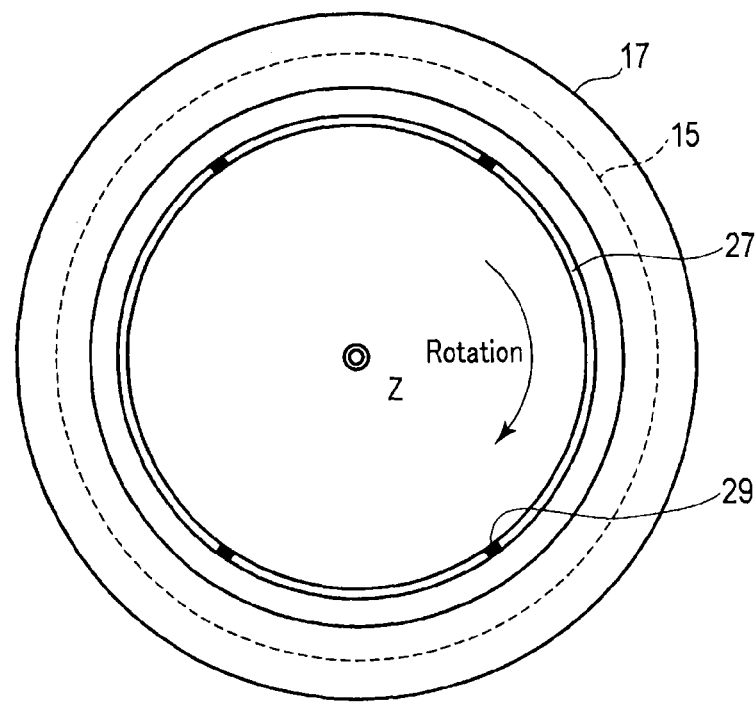
FIG. 5 is a schematic sectional view of a detector ring in FIG. 2.

FIG. 5 is a schematic sectional view of the detector ring 17. As shown in FIG. 5, the detector ring 17 includes the plurality of X-ray detectors 15 arrayed on a circumference. Each X-ray detector 15 detects X-rays from the X-ray source ring 13 and generates an electrical signal corresponding to the intensity of detected X-rays. The X-ray detector 15 may be a direct detection type semiconductor detector or an indirect type detector constituted by a scintillator and a photodetector. A plurality of collimators (to be referred to as post-collimators hereinafter) 27 are arranged outside the detector ring 17 on its inner circumferential side. Each post-collimator 27 is a structure made of an X-ray attenuation material for limiting the solid angle of incident X-rays on the X-ray detector 15. It is preferable to provide, as each post-collimator 27, a collimator having the same structure as that used in the current third-generation CT. The plurality of post-collimators 27 are supported by, for example, an annular support member (to be referred to as a collimator support member hereinafter) 29 so as to be rotatable about the central axis Z. The number of post-collimators 27 to be installed is not specifically limited as long as it is one or more. Typically, the number of post-collimators 27 to be installed is equal to the number of wedge filters 21, i.e., the number of directions in which irradiation is simultaneously performed from X-ray sources 11. In this case, angles around the rotation axis Z are called azimuth angles. For example, 0° corresponds to the highest position of the X-ray source ring 13 or detector ring 17, and 180° corresponds to the lowest position of the X-ray source ring 13 or detector ring 17. In this embodiment, the number of directions in which irradiation is simultaneously performed is the number of X-ray beams which are simultaneously applied and have different azimuth angles. In the case shown in FIG. 5, the number of post-collimators 27 installed is four. The collimator support member 29 is connected to a collimator driver 31. The collimator driver 31 generates motive power under the control of a collimator drive controller 65. Upon receiving the motive power, the collimator support member 29 rotates about the central axis Z at a constant angular velocity. The collimator support member 29 rotates independently of the detector ring 17. That is, the detector ring 17 remains stationary even when the collimator support member 29 rotates.

Figure 6:
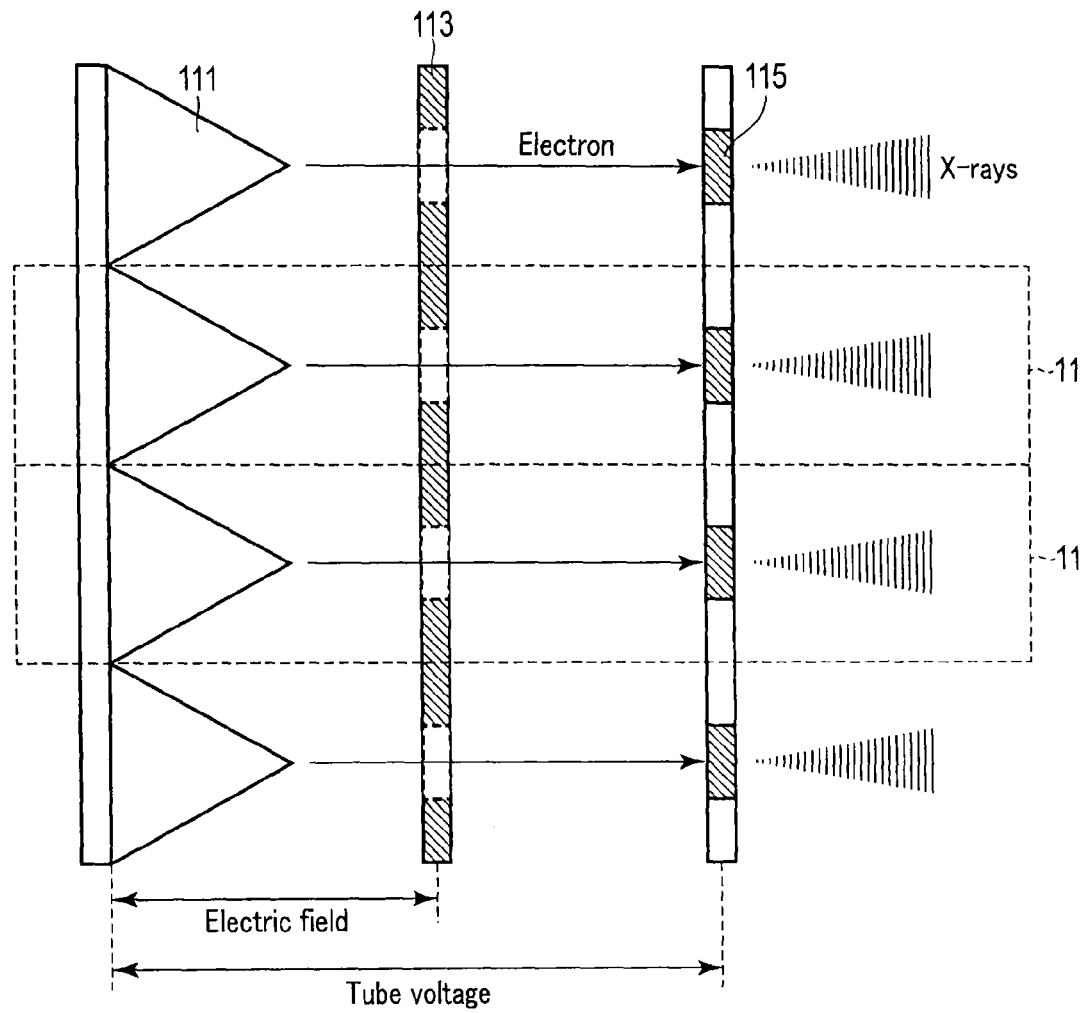
FIG. 6 is a view schematically showing the structure of an X-ray source in FIG. 1.

FIG. 6 is a view schematically showing the structure of each X-ray source 11. As shown in FIG. 6, the plurality of X-ray sources 11 are mounted on the X-ray source ring 13. Each X-ray source 11 includes a cold cathode electron source 111, a gate electrode 113, and an anode 115. The cold cathode electron source 111 is a material that emits electrons by using the field emission phenomenon. The field emission phenomenon is a phenomenon in which electrons in a metal placed in a high electric field exceed the work function and are emitted to the outside. A silicon or carbon nanotube is suitable as a material (to be referred to as an electric field emission material hereinafter) used for the cold cathode electron source 111. An electric field emission material is processed to have sharp tips, thereby forming a plurality of cold cathode electron sources 111. The plurality of cold cathode electron sources 111 are mounted on, for example, a semiconductor substrate. The plurality of cold cathode electron sources 111 are arranged to encircle the central axis Z inside the X-ray source ring 13.

As shown in FIG. 6, the plurality of gate electrodes 113 are arranged in front of the plurality of cold cathode electron sources 111. Each gate electrode 113 is an electrode for generating an electric field between itself and the cold cathode electron source 111. A gate driving circuit 33 is connected to each gate electrode 113. Each gate driving circuit 33 applies a gate pulse to the gate electrode 113 under the control of a gate controller 59. Upon receiving the gate pulse, the gate electrode 113 generates an electric field between itself and the cold cathode electron source 111. The cold cathode electron source 111 in an electric field emits an electron from its tip according to the field electron emission phenomenon. The plurality of gate electrodes 113 are mounted on a semiconductor substrate. The plurality of gate electrodes 113 are arranged to encircle the central axis Z inside the X-ray source ring 13.

As shown in FIG. 6, the anodes 115 are arranged at positions to face the cold cathode electron sources 111 through the gate electrodes 113. For example, the anodes 115 are arranged to squarely face the cold cathode electron sources 111. The plurality of anodes 115 are mounted on a semiconductor substrate. The plurality of anodes 115 are arranged to encircle the central axis Z inside the X-ray source ring 13. Upon receiving electrons from the cold cathode electron sources 111, the anodes 115 generate X-rays. The anodes 115 and the cold cathode electron sources 111 are connected to a high voltage generator 35. The high voltage generator 35 is provided for each X-ray source ring 13. More specifically, a high voltage generator 35-1 is connected to the X-ray source ring 13-1, and a high voltage generator 35-2 is connected to the X-ray source ring 13-2. The high voltage generator 35 applies tube voltages between the anodes 115 and the cold cathode electron sources 111 under the control of an X-ray controller 61. The electrons emitted from the cold cathode electron sources 111 fly to the anodes 115 upon reception of the tube voltages and collide with the anodes 115. The collision of electrons with the anodes 115 generates X-rays. The generated X-rays are applied on the opposite side of the cold cathode electron sources 111 through the gate electrodes 113. The X-rays emitted from the X-ray sources 11 fly to the X-ray detectors 15 located on the opposite side of the rotation axis Z to the X-ray sources 11. The X-ray detectors 15 then detect the X-rays. In other words, the cold cathode electron sources 111 and the anodes 115 are positioned such that generated X-rays travel to the X-ray detectors 15 located on the opposite side to the X-ray sources 11. In addition, the plurality of X-ray sources 11 mounted on the X-ray source ring 13-1 and the plurality of X-ray sources 11 mounted on the X-ray source ring 13-2 are positioned such that the X-rays applied from the X-ray source ring 13-1 are superimposed on the X-rays applied from the X-ray source ring 13-2 in the FOV. In other words, a spatial region where the X-rays applied from the X-ray source ring 13-1 are superimposed on the X-rays applied from the X-ray source ring 13-2 is set in the FOV.

Figure 7:
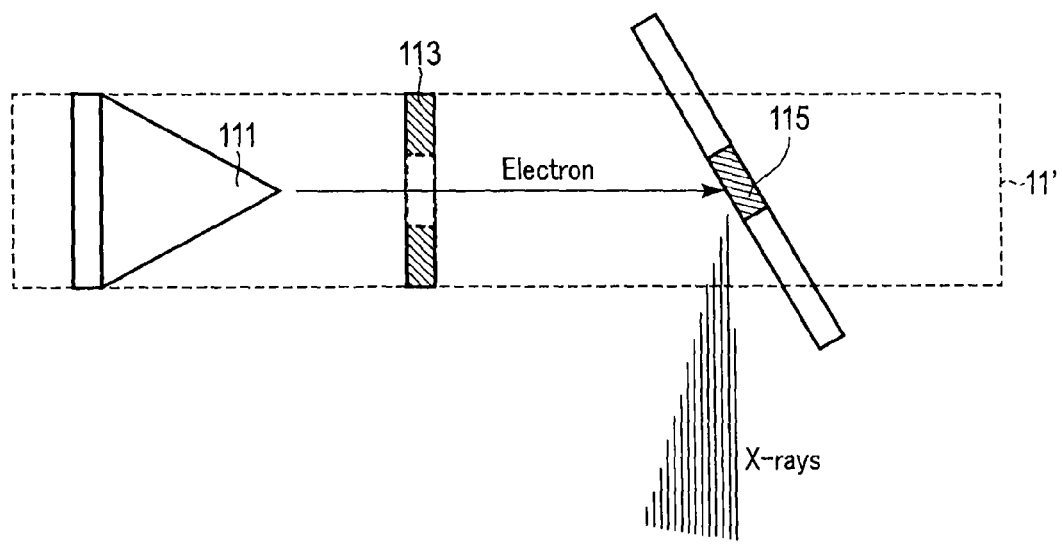
FIG. 7 is view schematically showing the structure of another X-ray source different from the X-ray source in FIG. 5.

Note that the arrangement of each X-ray source 11 in FIG. 6 is merely an example. For example, referring to FIG. 6 each anode 115 is arranged to squarely face an electron stream, i.e., is of a target transmission type. However, this embodiment is not limited to this. For example, as shown in FIG. 7 the anode 115 may be tilted with respect to an electron stream, i.e., may be of a target reflection type. Even in this case, the cold cathode electron source 111 and the anode 115 are positioned such that generated X-rays travel to the X-ray detector 15 located on the opposite side to the X-ray source 11.

In addition, referring to FIG. 6 each X-ray source 11 includes one each of the cold cathode electron source 111, the gate electrode 113, and the anode 115. However, this embodiment is not limited to this. It is possible to individually increase or decrease the numbers of cold cathode electron sources 111, gate electrodes 113, and anodes 115 of each X-ray source 11. For example, one anode 115 may be provided for a plurality of cold cathode electron sources 111 or a plurality of anodes 115 may be provided for one cold cathode electron source 111.

Figure 8:
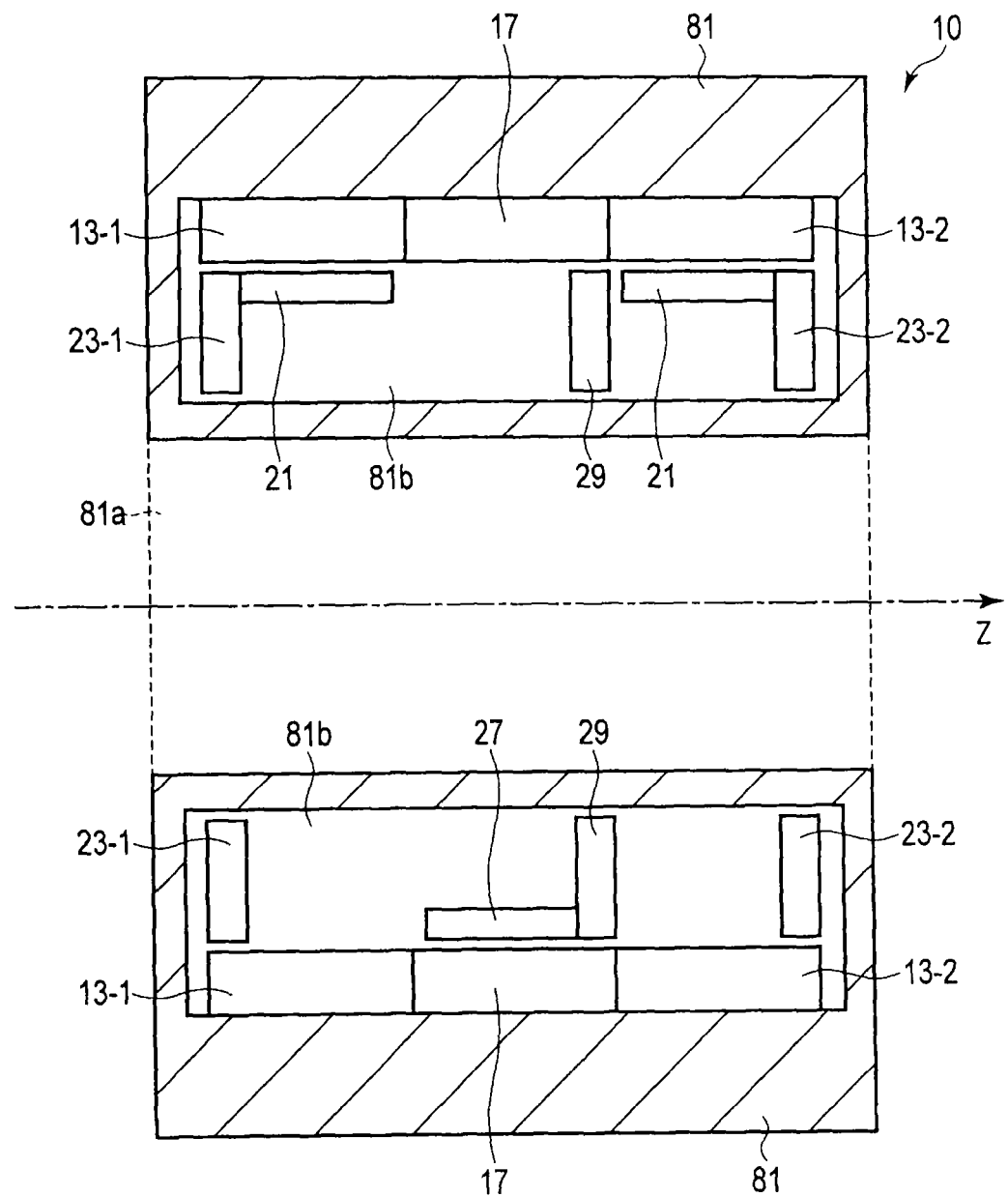
FIG. 8 is a longitudinal sectional view of a gantry according this embodiment.

The typical structure of the gantry 10 according to this embodiment will be described in more detail below. FIG. 8 is a longitudinal sectional view of the gantry 10 according to the embodiment. As shown in FIG. 8, the gantry 10 includes a housing 81 having an opening 81a. The X-ray source ring 13-1, the detector ring 17, and X-ray source ring 13-2 are arrayed in order in an internal space 81b of the housing 81 along the central axis Z. The filter support member 23-1 which supports at least one wedge filter 21 is arranged on the inner circumferential side of the X-ray source ring 13-1. Likewise, the filter support member 23-2 which supports at least one wedge filter 21 is arranged on the inner circumferential side of the X-ray source ring 13-2. Each filter support member 23 has an opening larger in diameter than the opening 81a and is arranged in the internal space 81b such that the central axis of the filter support member 23 coincides with the axis Z. Each filter support member 23 is preferably arranged on the opposite side of the central axis Z to the X-ray detection ring 17 so as not to block X-rays from each X-ray source ring 13. The collimator support member 29 which supports at least one post-collimator 27 is arranged on the inner circumferential side of the detector ring 17. The collimator support member 29 has an opening larger in diameter than the opening 81a and is arranged in the internal space 81b such that the central axis of the collimator support member 29 coincides with the axis Z. The filter driver 25 and the collimator driver 31 (neither of which is shown in FIG. 7) respectively rotate the filter support member 23 and the collimator support member 29 about the central axis Z.

Figure 9:
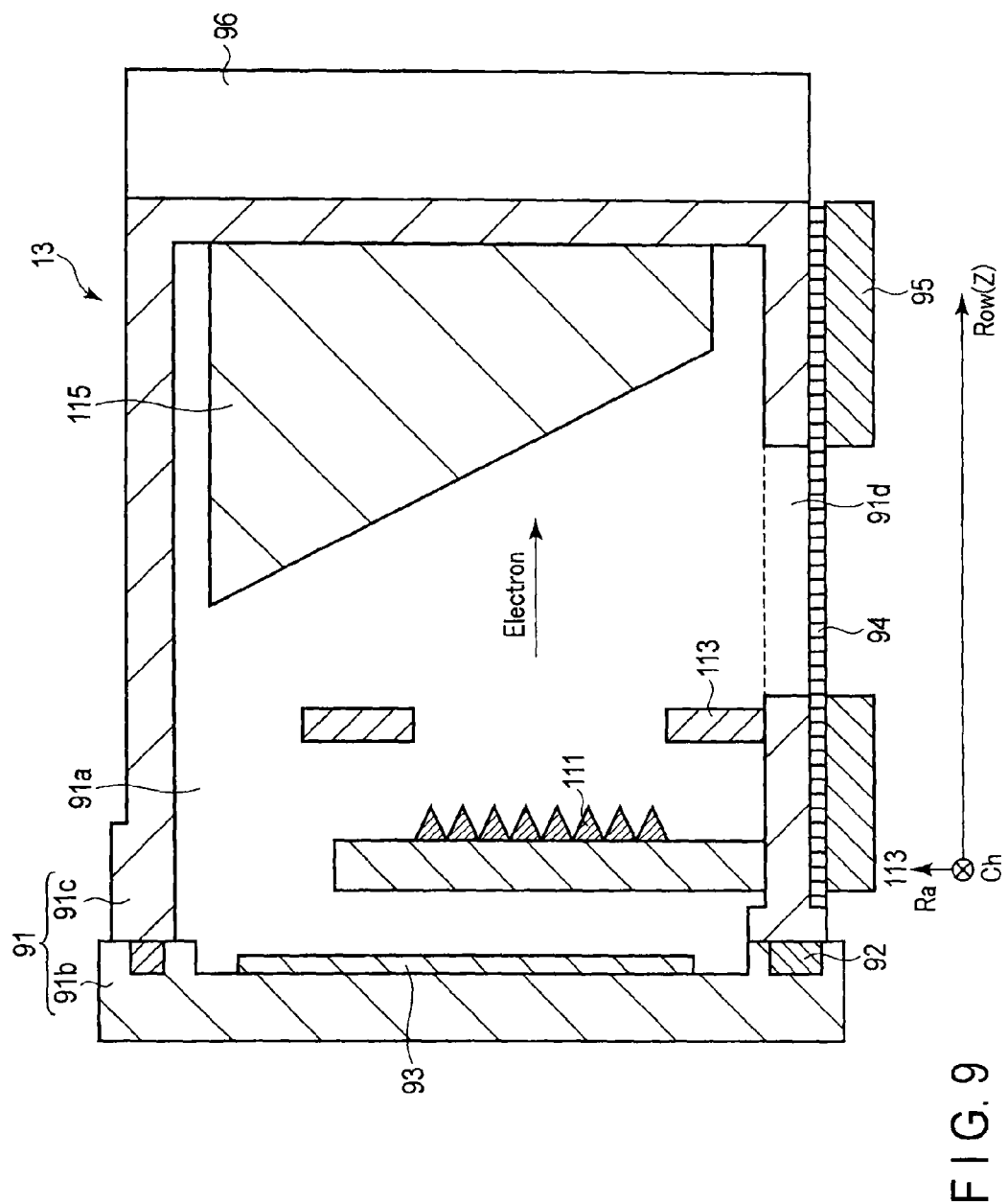
FIG. 9 is a longitudinal sectional view showing the detailed structure of the X-ray source ring in FIG. 7.

FIG. 9 is a longitudinal sectional view showing the detailed structure of each X-ray source ring 13. Note that a direction along the central axis Z of each X-ray source ring 13 will be referred to as a row direction (Row direction), and the circumferential direction of the X-ray source ring 13 will be referred to as a channel direction (Ch direction). A direction orthogonal to the row direction and channel direction coincides with the radial direction (Ra direction) of the X-ray source ring 13. As shown in FIG. 9, the X-ray source ring 13 includes a housing 91 having an annular shape whose central axis coincides with the central axis Z. The housing 91 has a hollow structure. A vacuum is maintained in an internal space 91a of the housing 91. More specifically, the housing 91 includes a lid 91b and a vessel 91c each having an annular shape whose central axis coincides with the axis Z. The lid 91b and the vessel 91c are preferably formed from a robust material such as iron or stainless steel. The lid 91b and the vessel 91c are preferably fastened to each other with a fastening tool or the like so as to accurately keep a vacuum in the internal space 91a. For example, the lid 91b and the vessel 91c are fastened to each other through a gasket 92. As the gasket 92 according to this embodiment, it is possible to use any of the existing types of gaskets such as a nonmetallic gasket, a semi-metallic gasket, and a metallic gasket. The inner surface of the lid 91b is provided with a getter 93 which adsorbs a residual gas in the internal space 91a. As the getter 93 according to this embodiment, it is possible to use either a contact getter or a diffusion getter. As the getter 93, for example, it is possible to use any of the existing metals such as titanium and a barium-aluminum alloy.

The plurality of cold cathode electron sources 111 are provided on the X-ray detection ring 17 side of the X-ray source ring 13. The plurality of cold cathode electron sources 111 are arrayed along the channel direction and the radial direction. For example, the plurality of cold cathode electron sources 111 are fixed to a support member 111a. The support member 111a is fixed to the inner surface of the vessel 91c. The anode 115 is provided on the opposite side to the plurality of cold cathode electron sources 111 in the row direction. The plurality of anodes 115 may be arrayed in the internal space 91a of the housing 91 along the channel direction or the anode 115 having an annular shape whose central axis coincides with the axis Z may be provided. To allow the anode 115 to irradiate the X-ray detection ring 17, which is adjacent to it along the central axis Z, with X-rays, the anode 115 is sloped so as to gradually decrease in thickness in the row direction toward the central axis Z along the radial direction. That is, the tilt direction of the anode 115 included in the X-ray source ring 13-1 is symmetric with that of the anode 115 included in the X-ray source ring 13-2 about the X-ray detection ring 17 as a boundary. The gate electrodes 113 are provided between the anode 115 and the plurality of cold cathode electron sources 111 in the row direction. The plurality of gate electrodes 113 are arrayed along the channel direction. When, for example, applying X-rays from 1,000 directions around the central axis Z, it is preferable to provide 1,000 gate electrodes 113 around the central axis Z. One gate electrode 113 is provided for a predetermined number of cold cathode electron sources 111 adjacent to each other in the channel direction. The predetermined number may be any number equal to or more than one. The gate electrodes 113 are fixed to, for example, the inner surface of the vessel 91c.

An exit port 91d for X-rays generated from the anode 115 is formed in the vessel 91c. The exit port 91d is formed in the vessel 91c so as to encircle the central axis Z. An X-ray filter 94 is attached to the outer wall of the vessel 91c so as to cover the exit port 91d. The X-ray filter 94 absorbs low-energy components of X-rays passing through the exit port 91d. The outer wall of the vessel 91c is provided with a slit 95 through the X-ray filter 94. The slit 95 limits the irradiation field of X-rays. Note that the slit 95 may be provided so as to be rotatable about the central axis Z in synchronism with the wedge filters 21.

The outer wall of the vessel 91c is provided with a cooling unit 96 which cools the X-ray source ring 13. As the cooling unit 96, it is possible to use any apparatus, tool, or material which can cool the X-ray source ring 13. For example, a cooling pipe through which a refrigerant passes can be used as the cooling unit 96. The main heat source of the X-ray source ring 13 is the anode 115 which generates heat upon receiving electrons from the cold cathode electron source 111. Therefore, the cooling unit 96 is preferably provided on the opposite side of the vessel 91c to the anode 115 to efficiently cool the anode 115.

As shown in FIG. 2, a data collection circuit 37 is connected to the plurality of X-ray detectors 15. The data collection circuit 37 reads out electrical signals generated by the plurality of X-ray detectors 15 under the control of an imaging controller 67, and converts the readout electrical signals into digital data by A/D conversion. More specifically, the data collection circuit 37 reads out electrical signals from the X-ray detectors 15 for each view and converts them into digital data. Digital data after conversion will be referred to as raw data. Raw data is supplied to the console 50. Note that a view corresponds to a sampling period for raw data from each X-ray detector 15 by the data collection circuit 37.

The gate controller 59 individually controls the plurality of gate driving circuits 33 so as to cause the plurality of X-ray sources 11 accommodated in the X-ray source ring 13-1 and the plurality of X-ray sources 11 accommodated in the X-ray source ring 13-2 to generate X-rays in a preset order under the control of the imaging controller 67. More specifically, the gate controller 59 supplies a timing pulse to the gate driving circuit 33 connected to the X-ray source 11 as an X-ray generation target. Upon receiving the timing pulse, the gate driving circuit 33 immediately applies a gate pulse to the gate electrode 113 for the X-ray source 11 as the connection destination. Upon application of the gate pulse, as described above, the cold cathode electron source 111 emits electrons according to the electric field emission phenomenon. The electrons then collide with the anode 115 to generate X-rays.

The order of generation of X-rays from the X-ray sources 11 (switching of the X-ray source 11 as an X-ray generation target) will be briefly described below. The X-ray source ring 13-1 and the X-ray source ring 13-2 alternately generate X-rays to prevent X-rays from the X-ray source ring 13-1 and X-rays from the X-ray source ring 13-2 from almost simultaneously entering the same X-ray detector 15.

The plurality of X-ray sources 11 in each X-ray source ring 13 are switched in the following manner. The X-ray source 11 as an X-ray generation target is switched among the plurality of X-ray sources 11 accommodated in each X-ray source ring 13 in accordance with a preset order for each view. The X-ray source 11 as an X-ray generation target is sequentially switched among the X-ray sources 11 along a circumference for each view. In this case, the gate controller 59 controls the plurality of gate driving circuits 33 so as to cause the plurality of X-ray sources 11 to sequentially generate X-rays around the circumference of the X-ray source ring 13. The X-ray generation targets are switched to the X-ray sources 11, of the plurality of X-ray sources 11 accommodated in the X-ray source ring 13-1 and of the plurality of X-ray sources 11 accommodated in the X-ray source ring 13-2, which are located at almost the same irradiation angle. With this switching control, each of the two X-ray source rings 13 sequentially generate X-rays around a circumference while X-rays are alternately generated from the two X-ray source rings 13.

Note that the gate driving circuits 33 may be driven to generate X-rays from one X-ray source 11 for each view or to generate X-rays from the plurality of X-ray sources 11 for each view. For example, it is preferable to drive the plurality of gate driving circuits 33 to simultaneously generate X-rays from the four X-ray sources 11 separated from each other at equal intervals for each view.

The X-ray controller 61 individually controls the high voltage generators 35-1 and 35-2 to apply a tube voltage corresponding to a predetermined X-ray condition between the cold cathode electron source 111 and the anode 115 under the control of the imaging controller 67. More specifically, the X-ray controller 61 supplies a timing pulse to the high voltage generator 35 to apply a tube voltage to the X-ray source 11 as an X-ray generation target in synchronism with the application of a gate pulse to the gate electrode 113. Upon receiving the timing pulse, the high voltage generator 35 immediately applies a tube voltage between the cold cathode electron source 111 and the anode 115 of the X-ray source 11 as the X-ray generation target. The electrons generated from the cold cathode electron source 111 upon application of the tube voltage collide with the anode 115 to generate X-rays. Note that a tube voltage application target is not limited to the X-ray source 11 as an X-ray generation target. That is, a tube voltage may be applied to the X-ray source 11 from which no X-rays are generated. Assume that X-ray conditions for the X-ray source ring 13-1 are typically almost the same as those for the X-ray source ring 13-2.

The filter drive controller 63 controls the filter driver 25-1 to rotate the plurality of wedge filters 21 supported by the filter support member 23-1 around the central axis Z and controls the filter driver 25-2 to rotate the plurality of wedge filters 21 supported by the filter support member 23-2 around the central axis Z under the control of the imaging controller 67. More specifically, the filter drive controller 63 supplies a driving pulse to the filter driver 25 in synchronism with the application of a gate pulse to the gate electrode 113 of the X-ray source 11 as an X-ray generation target, in other words, in synchronism with the generation of X-rays from the X-ray source 11. Upon receiving the driving pulse, the filter driver 25 drives the filter support member 23 to rotate the plurality of wedge filters 21 around the central axis Z at an angular velocity corresponding to the pulse interval between driving pulses. More specifically, the filter support member 23 is rotated to always position the wedge filter 21 in front of the X-ray source 11 as an X-ray generation target, which is switched for each view, regardless of switching of the X-ray 11. In other words, the filter support member 23 is rotated to position the wedge filter 21 in front of the X-ray generation portion of the X-ray source ring 13. The filter support member 23 may be continuously rotated or may be intermittently rotated to stop when X-rays are generated.

The collimator drive controller 65 controls the collimator driver 31 to rotate the plurality of post-collimators 27 around the central axis Z under the control of the imaging controller 67. More specifically, the collimator drive controller 65 supplies a driving pulse to the collimator driver 31 in synchronism with the application of a gate pulse to the gate electrode 113 of the X-ray source 11 as an X-ray generation target, in other words, in synchronism with the generation of X-rays from the X-ray source 11. Upon receiving the driving pulse, the collimator driver 31 drives the collimator support member 29 to rotate the plurality of post-collimators 27 around the central axis Z at an angular velocity corresponding to the pulse interval between driving pulses. More specifically, the collimator support member 29 is rotated to always set the post-collimator 27 in front of the X-ray detector 15 located on the opposite side of the central axis Z to the X-ray source 11 as an X-ray generation target, which is switched for each view, regardless of switching of the X-ray source 11. In other words, the collimator support member 29 is rotated to position the post-collimator 27 in front of the X-ray detector 15 located on the opposite side of the central axis Z to the X-ray generation portion of the X-ray source ring 13. The collimator support member 29 may be continuously rotated or may be intermittently rotated to stop when X-rays are generated.

As shown in FIG. 1, the console 50 includes a system controller 51 as a main unit, a preprocessor 53, a reconstruction unit 55, an image processor 57, the imaging controller 67, a display 69, an input unit 71, and a storage 73.

The preprocessor 53 preprocesses raw data from the data collection circuit 37. As preprocessing, the same processing as that used in the third-generation CT is used. More specifically, preprocessing includes logarithmic conversion, X-ray intensity correction, and offset correction.

The reconstruction unit 55 generates a CT image expressing the spatial distribution of CT values by applying an image reconstruction algorithm for raw data after preprocessing. As an image reconstruction algorithm, there may be used any of the existing image reconstruction algorithms including analytical image reconstruction methods such as the FBP (filtered back projection) method and the CBP (convolution back projection) method and statistical image reconstruction methods such as the ML-EM (maximum likelihood expectation maximization) method and the OS-EM (ordered subset expectation maximization) method.

The image processor 57 performs various types of image processing for a CT image. For example, the image processor 57 performs volume rendering, surface rendering, pixel value projection processing, pixel value conversion, and the like.

The imaging controller 67 synchronously controls the gate controller 59, the X-ray controller 61, the filter drive controller 63, the collimator drive controller 65, and the data collection circuit 37. More specifically, the imaging controller 67 synchronously outputs commands to the gate controller 59 and the X-ray controller 61 to switch the X-ray source 11 as an X-ray generation target in synchronism with the switching of a view. In addition, the imaging controller 67 synchronously outputs commands to the filter drive controller 63 and the collimator drive controller 65 to place the wedge filter 21 in front of the X-ray source 11 as an X-ray generation target and to place the post-collimator 27 in front of the X-ray detector 15 located on the opposite side of the central axis Z to the X-ray source 11. In other words, the imaging controller 67 synchronously outputs commands to the filter drive controller 63 and the collimator drive controller 65 to position the wedge filter 21 in front of the X-ray generation portion of the X-ray source ring 13 and position the post-collimator 27 in front of the X-ray detector 15 located on the opposite side of the central axis Z to the X-ray generation portion. In addition, the imaging controller 67 controls the data collection circuit 37 to read out electrical signals from the X-ray detector 15 in synchronism with the switching of a view. The switching timing of a view may be defined by the timing at which the filter support member 23 or the collimator support member 29 generates a trigger signal every time the filter support member 23 or the collimator support member 29 rotates through a predetermined angle or may be defined by the generation timing of a frequency division signal of a clock signal from a clock circuit of the imaging controller 67 (or the system controller 51).

The display 69 displays various types of information. For example, the display 69 displays the CT image generated by the reconstruction unit 55, a CT image after image processing by the image processor 57, or the like. In addition, the display 69 displays a setting screen for imaging conditions or the like. As a display 69, it is possible to use, for example, a CRT display, liquid crystal display, organic EL display, or plasma display.

The input unit 71 accepts various types of commands or information inputs from the user of an input device. As an input device, it is possible to use a keyboard, a mouse, various types of switches, and the like.

The storage 73 is a storage device which stores various types of information. For example, the storage 73 stores raw data and CT images. In addition, the storage 73 stores an imaging program according to this embodiment.

The system controller 51 functions as the main unit of the X-ray computed tomography apparatus. The system controller 51 reads out an imaging program according to this embodiment from the storage, and controls various types of constituent elements in accordance with the imaging program, thereby performing imaging processing according to the embodiment.

An operation example in imaging processing performed by the X-ray computed tomography apparatus under the control of the system controller 51 will be described next. Imaging processing using the single X-ray source ring 13 will be described first.

FIGS. 10A and 10B are plan views showing the placement of the X-ray source 11 of each X-ray source ring 13, the wedge filter 21, and the post-collimator 27 when the number of directions in which irradiation is simultaneously performed is one. FIG. 10A shows the placement at time t. FIG. 10B shows the placement at time t+Δt. The imaging controller 67 synchronously controls the gate controller 59, the X-ray controller 61, the filter drive controller 63, the collimator drive controller 65, and the data collection circuit 37 so as to sequentially switch the X-ray source 11 as an X-ray generation target around the central axis Z, place the wedge filter 21 in front of the X-ray source 11 as the X-ray generation target, and place the post-collimator 27 in front of the X-ray detector 15 facing the X-ray source 11 as the X-ray generation target. In this case, the plurality of X-ray sources 11 and the plurality of X-ray detectors 15 are fixed without being rotated.

More specifically, in an imaging period, the X-ray source 11 as an X-ray generation target is sequentially switched along an circumference for each set of a predetermined number of views so as to apply X-rays from the entire angle range necessary for image reconstruction. When, for example, 360° reconstruction is to be performed, an X-ray source as an X-ray generation target is sequentially and electrically switched along the circumference for each set of a predetermined number of views so as to apply X-rays from all directions in an imaging period. The wedge filter 21 and the post-collimator 27 rotate in synchronism with the switching of the X-ray source 11 so as to place the wedge filter 21 in front of the X-ray source 11 as an X-ray generation target and place the post-collimator 27 in front of the X-ray detector 15 facing the X-ray source 11 over an imaging period.

The data collection circuit 37 collects the electrical signals generated by the X-ray detectors 15. For example, the data collection circuit 37 collects data (to be referred to as an intensity value record hereinafter) representing a digital value (to be referred to as an intensity value hereinafter) corresponding to the intensity of X-rays for each address (a combination of a channel and a row) of the X-ray detector which has detected the X-rays. The data collection circuit 37 generates a set of intensity value records concerning all addresses associated with the same azimuth angle as raw data. When raw data in an angle range necessary for image reconstruction is collected in this manner, the imaging controller 67 terminates the imaging operation. The preprocessor 53 then performs preprocessing for the raw data. Then reconstruction unit 55 generates a CT image based on the raw data after the preprocessing. The display 69 displays the generated CT image.

Even the X-ray computed tomography apparatus including the X-ray source ring 13 and the detector ring 17 can perform CT imaging similar to that in third-generation CT by moving the X-ray generation portion along a circumference by electrically switching the gate electrodes 113 upon fixing the spatial positions of the plurality of X-ray sources 11 arrayed on the circumference. The gate controller 59 switches the gate electrodes 113 at high speed. The X-ray computed tomography apparatus according to this embodiment can therefore shorten the imaging time as compared with the third-generation CT designed to rotate a heavy rotating ring as in the related art. In addition, as in third-generation CT, the X-ray computed tomography apparatus according to the embodiment can suppress the exposure dose of the subject S and reduce the amount of scattered radiation detected by rotating the wedge filter 21 and the post-collimator 27 in synchronism with the switching of the X-ray source 11. Note that the filter support member 23 equipped with the wedge filters 21 and the collimator support member 29 equipped with the post-collimators 27 are lighter in weight than the rotating ring in the third-generation CT, which is equipped with an X-ray tube, a high voltage generator, an X-ray detector, and the like. The centrifugal force accompanying the rotation of the filter support member 23 and the collimator support member 29 is lower than that accompanying the rotation of the rotating ring in the third-generation CT. The X-ray computed tomography apparatus according to this embodiment can therefore rotate the filter support member 23 and the collimator support member 29 at a high speed corresponding to the switching speed of the gate electrode 113.

Figure 11A:
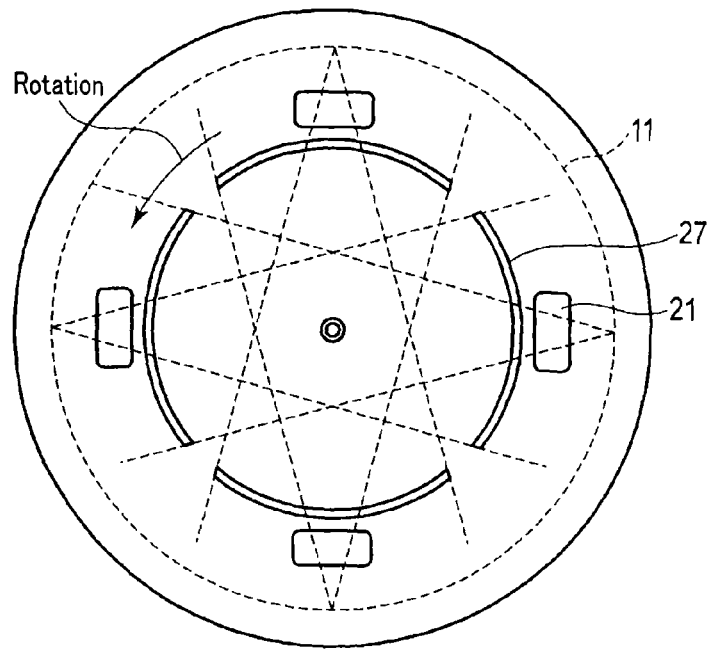
FIG. 11A is a plan view showing the placement of X-ray sources, wedge filters, and post-collimators at time t when the number of X-ray sources simultaneously driven is four according to the first embodiment.
Figure 11B:
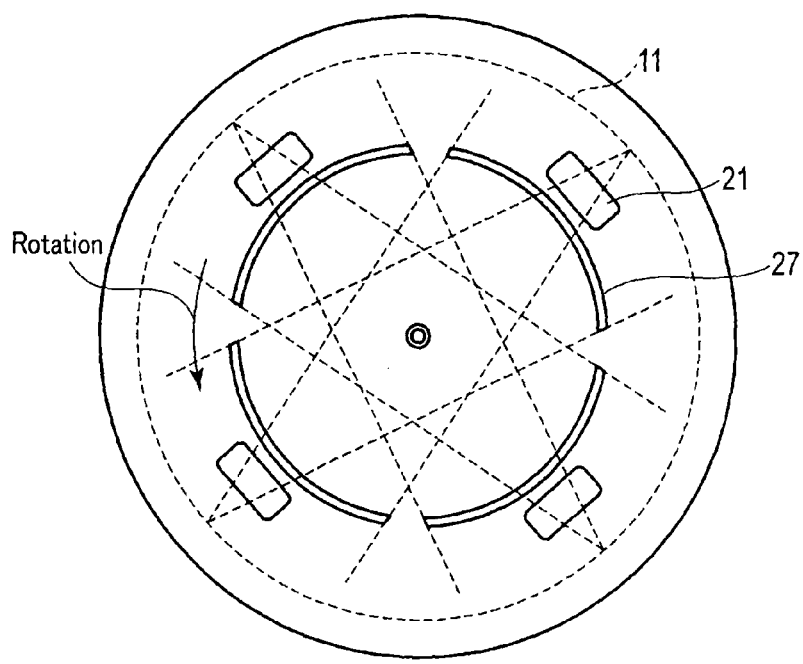
FIG. 11B is a plan view showing the placement of the X-ray sources, the wedge filters, and the post-collimators at time t+Δt when the number of X-ray sources simultaneously driven is four according to the first embodiment.

An operation example concerning each X-ray source ring 13 when the number of directions in which irradiation is simultaneously performed is four will be described next. FIGS. 11A and 11B are plan views each showing the placement of the X-ray sources 11 of each X-ray source ring 13, the wedge filters 21, and the post-collimators 27 when the number of directions in which irradiation is simultaneously performed is four. FIG. 11A shows the placement at time t. FIG. 11B shows the placement at time t+Δt. A combination of the X-ray source 11, the wedge filter 21, and the post-collimator 27 serves as one X-ray irradiation system in CT. Simultaneously performing irradiation in four directions is synonymous with having four X-ray irradiation systems. Referring to FIGS. 11A and 11B, the four X-ray sources 11 as X-ray generation targets are set to be separated from each other at 90° intervals for each view. The imaging controller 67 synchronously controls the gate controller 59, the X-ray controller 61, the filter drive controller 63, the collimator drive controller 65, and the data collection circuit 37 to sequentially switch the four X-ray sources 11 as X-ray generation targets along the circumference, respectively arrange the wedge filters 21 in front of the four X-ray sources 11, and respectively arrange the post-collimators 27 in front of the X-ray detectors 15 each located on the opposite side of the central axis Z to a corresponding one of the X-ray sources 11. In this case, the plurality of X-ray sources 11 and the plurality of X-ray detectors 15 are fixed without being rotated.

More specifically, the X-ray sources 11 as X-ray generation targets are sequentially switched along the circumference for each set of a predetermined number of views so as to apply X-rays from all the angle ranges necessary for image reconstruction. When, for example, 360° reconstruction is to be performed, the X-ray sources 11 as X-ray generation targets are sequentially switched along the circumference for each set of a predetermined number of views so as to apply X-rays from all directions in an imaging period. Note that the predetermined number of views can be set to an arbitrary number equal to or more than one. The four wedge filters 21 and the four post-collimators 27 are rotated in synchronism with the switching of the X-ray sources 11 as X-ray generation targets so as to respectively arrange the four wedge filters 21 in front of the four X-ray sources 11 as the X-ray generation targets and respectively arrange the four post-collimators 27 in front of the four X-ray detectors 15 each located on the opposite side to a corresponding one of the four X-ray sources 11 as the X-ray generation targets over an imaging period.

When the number of directions in which irradiation is simultaneously performed is four, it is possible to shorten the imaging time to ¼ that when the number of directions in which irradiation is simultaneously performed is one, by using the same material for all the wedge filters 21 and all the post-collimators 27 and applying the same tube voltage to all the X-ray sources 11. In addition, when rotating the wedge filters 21 and the post-collimators 27 at the same rotational speed as that in the current third-generation CT, it is possible to shorten the imaging time to 70 ms or less. This makes it possible to execute cardiac CT with respect to even the subject S with a heartbeat of 100 or more without any medication. As described above, the X-ray computed tomography apparatus according to this embodiment can greatly reduce the weight of the rotating portion as compared with the third-generation CT, and hence can implement imaging at a high speed of 50 ms or less when rotating the wedge filters 21 and the post-collimators 27 with the same centrifugal force as that in the current third-generation CT.

The data collection circuit 37 collects the electrical signals generated by the X-ray detectors 15 as raw data. For example, the data collection circuit 37 collects an intensity value record representing a digital value (intensity value) corresponding to the intensity of X-rays for each of the addresses of the X-ray detectors 15 which have detected the X-rays. The data collection circuit 37 generates a set of intensity value records concerning all addresses associated with the same azimuth angle as raw data. When raw data in an angle range necessary for image reconstruction is collected in this manner, the imaging controller 67 terminates the imaging operation. The preprocessor 53 then performs preprocessing for the raw data. Then reconstruction unit 55 generates a CT image based on the raw data after the preprocessing. The display 69 displays the generated CT image.

An operation example in imaging processing using the two X-ray source rings 13 will be described next.

Figure 12A:
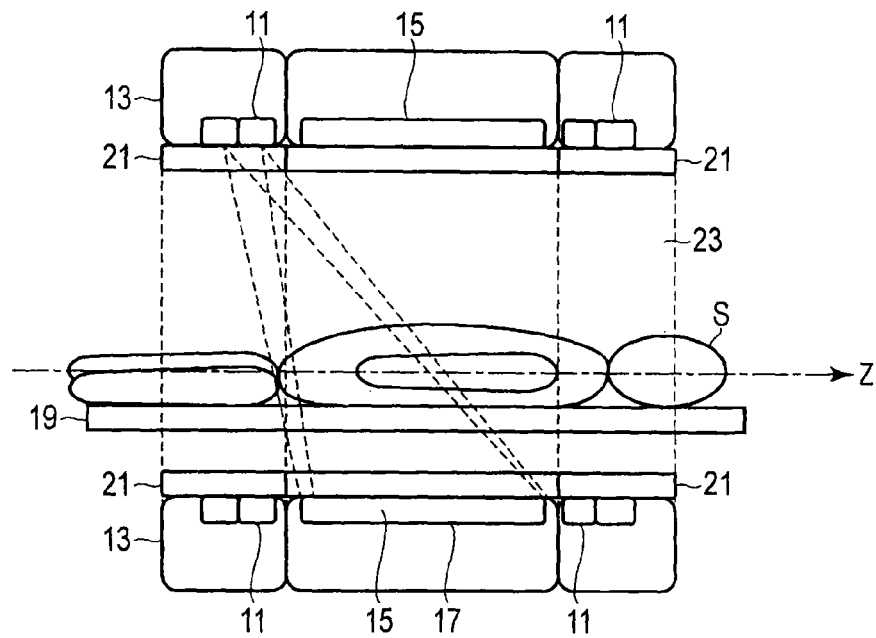
FIG. 12A is a view schematically showing an X-ray generation timing in imaging processing using two X-ray source rings according to the first embodiment, and a view showing the generation of X-rays in a view n.
Figure 12B:
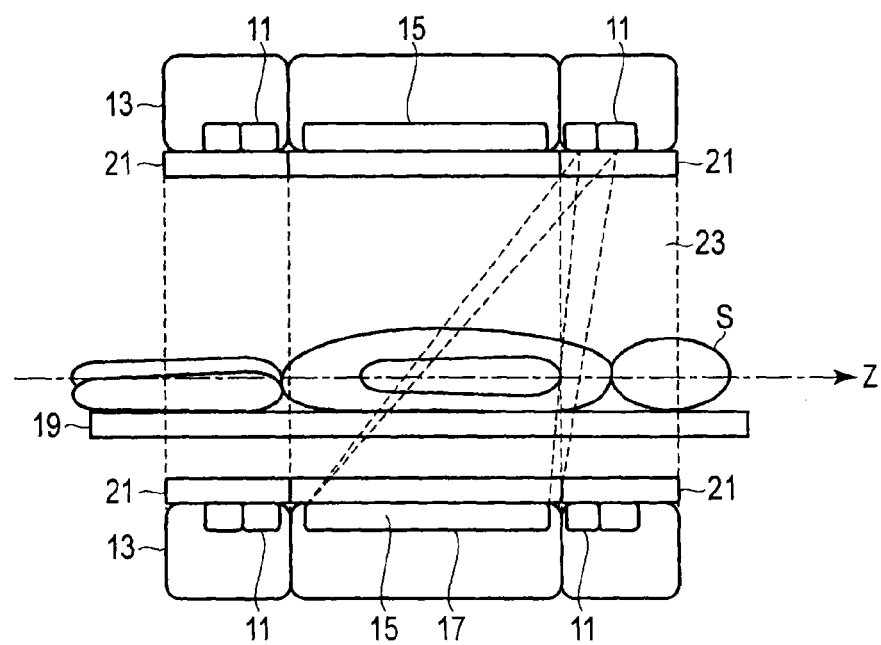
FIG. 12B is a view schematically showing an X-ray generation timing in imaging processing using two X-ray source rings according to the first embodiment, and a view showing the generation of X-rays in a view n+1.

FIGS. 12A and 12B are views each schematically showing the X-ray generation timing in imaging processing using the two X-ray source rings 13. FIG. 12A shows the generation of X-rays in a view n. FIG. 12B shows the generation of X-rays in a view n+1. Note that n is an integer. In addition, referring to FIGS. 12A and 12B, for the sake of simplicity, assume that the number of directions in which X-ray irradiation is simultaneously performed is one. However, even when using two X-ray source rings 13, it is possible to set the number of directions in which X-ray irradiation is simultaneously performed to an arbitrary number equal to or more than two. As shown in FIG. 12A, X-rays are generated from the X-ray source 11 at an azimuth angle on the X-ray source ring 13-1 in the view n. Subsequently, as shown in FIG. 12B, X-rays are generated from the X-ray source 11 at the same azimuth angle on the X-ray source ring 13-2 in the view n+1. When, for example, X-rays are generated from the X-ray source 11 at an azimuth angle of 0° on the X-ray source ring 13-1 in the view n, X-rays are generated from the X-ray source 11 at an azimuth angle of 0° on the X-ray source ring 13-2 in the next view n+1. Although the angle of X-rays from the X-ray source ring 13-1 around the central axis Z is the same as that of X-rays from the X-ray source ring 13-2, their tilt angles with respect to the central axis Z (more specifically, the angles of the center lines of X-rays with respect to the axis Z; to be simply referred to as tilt angles hereinafter) differ from each other. The imaging controller 67 synchronously controls the gate controller 59 and the X-ray controller 61 to alternately generate X-rays from the X-ray source ring 13-1 and the X-ray source ring 13-2 while sequentially switching the X-ray sources 11 as X-ray generation targets on the X-ray source ring 13-1 and the X-ray source ring 13-2 in the circumferential direction.

Note that in the above imaging example, in the view n and the subsequent view n+1, the X-ray source 11 as an X-ray generation target on the X-ray source ring 13-1 is located at the same azimuth angle as that of the X-ray source 11 as an X-ray generation target on the X-ray source ring 13-2. However, this embodiment is not limited to this. In the view n and the subsequent view n+1, the X-ray source 11 as an X-ray generation target on the X-ray source ring 13-1 may be located at an azimuth angle different from that of the X-ray source 11 as an X-ray generation target on the X-ray source ring 13-2. The user can individually set the order of generation of X-rays from each X-ray source ring 13 to an arbitrary order of generation.

The data collection circuit 37 collects the electrical signals generated by the X-ray detectors 15. For example, the data collection circuit 37 collects data (an intensity value record) representing a digital value (an intensity value) corresponding to the intensity of X-rays for each address (a combination of a channel and a row) of the X-ray detector 15 which has detected the X-rays. The data collection circuit 37 generates a set of intensity value records concerning all addresses for each combination of an azimuth angle and a tilt angle. In the present application, the imaging controller 67 switches a view for each combination of an azimuth angle and a tilt angle. When raw data in an angle range necessary for image reconstruction is collected in this manner, the imaging controller 67 terminates the imaging operation. The preprocessor 53 then performs preprocessing for the raw data. Then reconstruction unit 55 generates a CT image based on the raw data after the preprocessing. More specifically, the reconstruction unit 55 reconstructs a CT image targeting at an FOV based on both raw data originating from X-rays from the X-ray source ring 13-1 and raw data originating from X-rays from the X-ray source ring 13-2. The display 69 displays the generated CT image.

In the above embodiment, X-rays are alternately generated from the X-ray source ring 13-1 and the X-ray source ring 13-2. However, this embodiment is not limited to this. X-rays may be simultaneously generated from the X-ray source ring 13-1 and the X-ray source ring 13-2.

Figure 13:
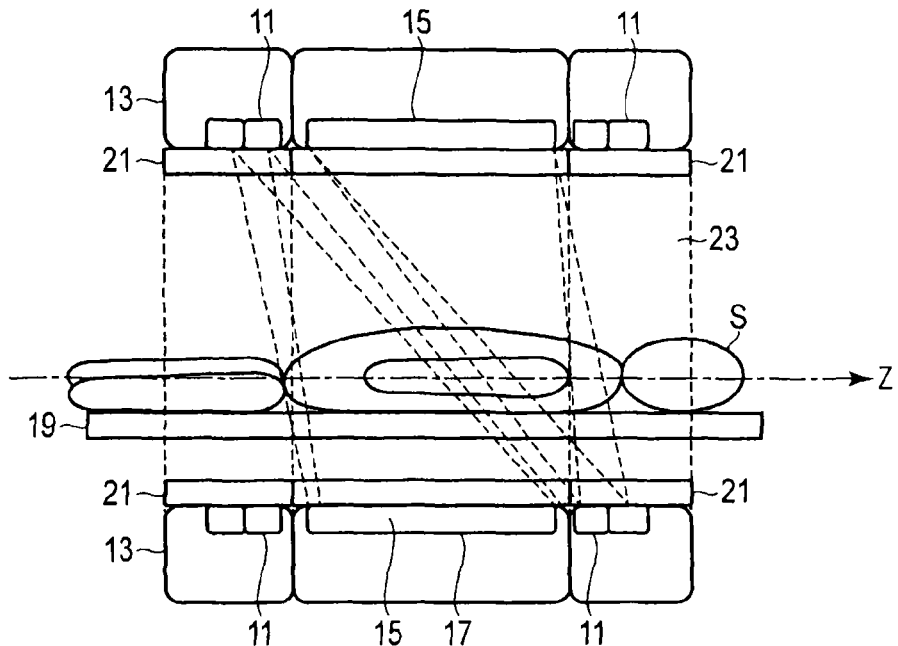
FIG. 13 is another view schematically showing an X-ray generation timing in imaging processing using two X-ray source rings according to the first embodiment.

FIG. 13 is another view schematically showing the X-ray generation timing in imaging processing using the two X-ray source rings 13. As shown in FIG. 13, X-rays may be simultaneously generated from the X-ray source ring 13-1 and the X-ray source ring 13-2. In simultaneous X-ray irradiation, the frequency of generation of scattered X-rays increases. Scattered X-rays degrade image quality. In order to reduce the frequency of generation of scattered X-rays, the azimuth angle difference between the X-ray source 11 as an X-ray generation target on the X-ray source ring 13-1 and the X-ray source 11 as an X-ray generation target on the X-ray source ring 13-2 is preferably set to 90° or more. Preferably, as shown in FIG. 13, the azimuth angle difference between the X-ray source 11 as an X-ray generation target on the X-ray source ring 13-1 and the X-ray source 11 as an X-ray generation target on the X-ray source ring 13-2 is preferably set to 180° to minimize the frequency of generation of scattered X-rays. An azimuth angle difference can be arbitrarily set via the input unit 71. The imaging controller 67 synchronously controls the gate controller 59 and the X-ray controller 61 to simultaneously generate X-rays from the X-ray source ring 13-1 and the X-ray source ring 13-2 while maintaining the set azimuth angle difference and sequentially switching the X-ray source 11 as an X-ray generation target on the X-ray source ring 13-1 and the X-ray source 11 as an X-ray generation target on the X-ray source ring 13-2 around the circumference.

When simultaneously applying X-rays from the X-ray source ring 13-1 and the X-ray source ring 13-2, it is possible to shorten the imaging time as compared with the case in which X-rays are alternately applied from the X-ray source ring 13-1 and the X-ray source ring 13-2. When alternately applying X-rays from the X-ray source ring 13-1 and the X-ray source ring 13-2, it is possible to reduce the frequency of generation of scattered X-rays, i.e., improve the image quality as compared with the case in which X-rays are simultaneously applied from the X-ray source ring 13-1 and the X-ray source ring 13-2. It is possible to arbitrarily set the mode of simultaneously applying X-rays from the X-ray source ring 13-1 and the X-ray source ring 13-2 and the mode of alternately applying X-rays in consideration of the balance between time and image quality.

As described above, the imaging controller 67 according to this embodiment synchronously controls the gate controller 59 and the X-ray controller 61 to cause each of the X-ray source ring 13-1 and the X-ray source ring 13-2 to generate X-rays while switching between azimuth angles sequentially around the circumference and also cause the X-ray source ring 13-1 and the X-ray source ring 13-2 to alternately generate X-rays for each azimuth angle. Alternately generating X-rays at different tilt angles at the same imaging angle can implement flying focus scanning in a simulated manner. That is, imaging using the two X-ray source rings 13 according to the present application can increase the number of X-rays per unit space at each imaging angle and eventually improve the spatial resolution in the central axis Z direction as compared with a case in which imaging is performed by using a single X-ray source ring. Therefore, the imaging controller 67 according to the embodiment can improve the spatial resolution of a CT image as compared when using a single X-ray source ring.

Note that in the above embodiment, the gate controller 59, the X-ray controller 61, the filter drive controller 63, and the collimator drive controller 65 are provided in the gantry 10. However, this embodiment is not limited to this. That is, some or all of the gate controller 59, the X-ray controller 61, the filter drive controller 63, and the collimator drive controller 65 may be provided in the console 50.

Application Example

In the above embodiment, even if the number of directions in which irradiation is simultaneously performed is plural, single-energy CT is executed. However, this embodiment is not limited to this. An X-ray computed tomography apparatus according to an application example of this embodiment can execute spectral CT (multi-energy CT) when the number of directions in which irradiation is simultaneously performed is plural. The X-ray computed tomography apparatus according to this application example will be described below.

The X-ray computed tomography apparatus according to this embodiment can execute tube-voltage-based spectral CT and filter-based spectral CT using each of the two X-ray source rings 13. The X-ray computed tomography apparatus according to the embodiment individually executes spectral CT by using the two X-ray source rings 13. Tube-voltage-based spectral CT will be described first. Note that the X-ray computed tomography apparatus according to the embodiment can perform spectral CT without any limitation on the number of directions in which irradiation is simultaneously performed. However, for the sake of a concrete description of the embodiment, assume that the number of directions in which irradiation is simultaneously performed from X-ray sources is three. Note that the execution of spectral CT using one of the two X-ray source rings 13 is the same as that using the other X-ray source ring 13. The execution of spectral CT using one X-ray source ring 13 will be described unless otherwise specified.

Figure 14:
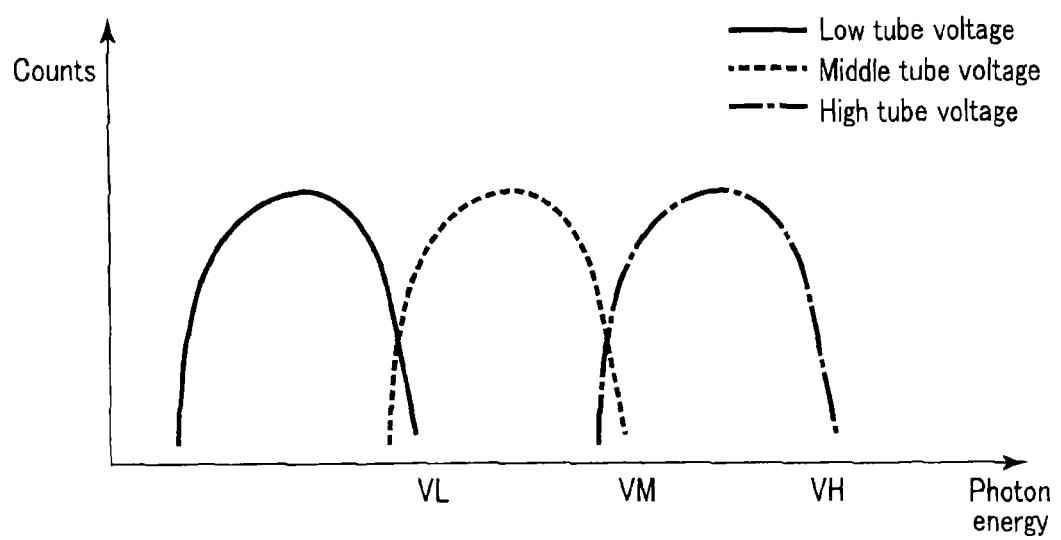
FIG. 14 is a graph schematically showing the energy spectra of X-rays generated from an X-ray source upon application of different tube voltages according to an application example of the first embodiment.

FIG. 14 is a graph schematically showing the energy spectra of X-rays generated from the X-ray source 11 upon reception of different tube voltages. The ordinate of FIG. 14 is defined as the counts of X-rays entering the X-ray detector 15. The abscissa of FIG. 14 is defined as photon energy. The solid line in FIG. 14 represents the energy spectrum of X-rays generated from the X-ray source 11 upon reception of a low tube voltage, and represents an energy distribution corresponding to the low tube voltage, with an energy value VL being the maximum. Likewise, the dotted line in FIG. 14 represents the energy spectrum of X-rays generated from the X-ray source 11 upon reception of a middle tube voltage, and represents an energy distribution corresponding to the middle tube voltage, with an energy value VM being the maximum. The one-dot dashed line in FIG. 14 represents the energy spectrum of X-rays generated from the X-ray source 11 upon reception of a high tube voltage, and represents an energy distribution corresponding to the high tube voltage, with an energy value VH being the maximum. Note that the low tube voltage, the middle tube voltage, and the high tube voltage increase in value in the order named. Discretely setting a plurality of tube voltage values for the plurality of X-ray sources 11 in this manner will separate the energy ranges of X-rays generated from the plurality of X-ray sources 11 from each other. This makes it possible to perform spectral CT.

FIGS. 15A and 15B are plan views each showing the placement of the X-ray sources 11, the wedge filters 21, and the post-collimators 27 when the number of directions in which irradiation is simultaneously performed is three in tube-voltage-based spectral CT. FIG. 15A shows the placement at time t. FIG. 15B shows the placement at time t+Δt. As described above, when the number of directions in which irradiation is simultaneously performed is three, the three wedge filters 21 are held by the filter support member 23 along a circumference at equal intervals, and the three post-collimators 27 are held by the collimator support member 29. The three wedge filters 21 are formed from the same material to make them exhibit the same X-ray attenuation effect with respect to X-rays from the three X-ray sources 11.

When performing tube-voltage-based spectral CT, the imaging controller 67 synchronously controls the gate controller 59, the filter drive controller 63, the collimator drive controller 65, and the data collection circuit 37, with respect to each of the two X-ray source rings 13, to sequentially switch the three X-ray sources as X-ray generation targets along a circumference, arrange the wedge filter 21 in front of each of the three X-ray sources 11 as X-ray generation targets, and arrange the post-collimator 27 in front of each X-ray detector 15 located on the opposite side of the central axis Z to a corresponding one of the X-ray sources 11 as X-ray generation targets. In this case, the imaging controller 67 controls the gate controller 59 and the X-ray controller 61, with respect to each of the two X-ray source rings 13, to perform X-ray irradiation in the same angle range necessary for image reconstruction with each of three tube voltages. When, for example, in the case of 360° reconstruction, X-ray irradiation is performed throughout 360° starting from each of different angles with three tube voltages, with respect to each of the two X-ray source rings 13. In the case shown in FIG. 12, low-tube-voltage X-rays is irradiated in the angle range of 0° to 360°, middle-tube-voltage X-rays is irradiated in the angle range of 120° to 480°, and high-tube-voltage X-rays is irradiated in the angle range of 240° to 600°.

The data collection circuit 37 collects raw data from each X-ray detector 15 for each view. In this case, raw data originating from the X-rays generated from the X-ray source 11 upon application of a high tube voltage is called high-tube-voltage raw data, raw data originating from the X-rays generated from the X-ray source 11 upon application of a middle tube voltage is called middle-tube-voltage raw data, and raw data originating from the X-rays generated from the X-ray source 11 upon application of a low tube voltage is called low-tube-voltage raw data. The reconstruction unit 55 reconstructs a CT image (high-tube-voltage CT image) based on high-tube-voltage raw data, a CT image (middle-tube-voltage CT image) based on middle-tube-voltage raw data, and a CT image (low-tube-voltage CT image) based on low-tube-voltage raw data. In addition, the reconstruction unit 55 may generate an image concerning a base material (a base material image) based on high-tube-voltage raw data, middle-tube-voltage raw data, and low-tube-voltage raw data or may generate a monochromatic X-ray image, a density image, and an effective atomic number image, each based on the base material. The display 69 displays the high-tube-voltage CT image, middle-tube-voltage CT image, low-tube-voltage CT image, base material image, monochromatic X-ray image, density image, and effective atomic number image.

With the above arrangement, the X-ray computed tomography apparatus including the two X-ray source rings 13 and the detector ring 17 implements tube-voltage-based spectral CT with respect to each of the two X-ray source rings 13.

Filter-based spectral CT will be described next. FIG. 16 is a graph schematically showing the energy spectra of X-rays generated from the X-ray sources 11 and transmitted through the wedge filters 21 with different X-ray attenuation coefficients. The ordinate of FIG. 16 is defined as the counts of X-rays entering the X-ray detector 15. The abscissa of FIG. 16 is defined as photon energy. The solid line in FIG. 16 represents the energy spectrum of X-rays transmitted through the wedge filter 21 with a low X-ray attenuation coefficient, and represents an energy distribution with the energy value VL being the maximum. Likewise, the dotted line represents the energy spectrum of X-rays transmitted through the wedge filter 21 with a middle X-ray attenuation coefficient, and represents an energy distribution with the energy value VM being the maximum. The one-dot dashed line in FIG. 16 represents the energy spectrum of X-rays transmitted through the wedge filter 21 with a high X-ray attenuation coefficient, and represents an energy distribution with the energy value VH being the maximum. Discretely setting a plurality of X-ray attenuation coefficients for the plurality of wedge filters 21 in this manner will separate the energy ranges of X-rays transmitted through the plurality of wedge filters 21 from each other. This makes it possible to perform spectral CT.

Figure 17A:
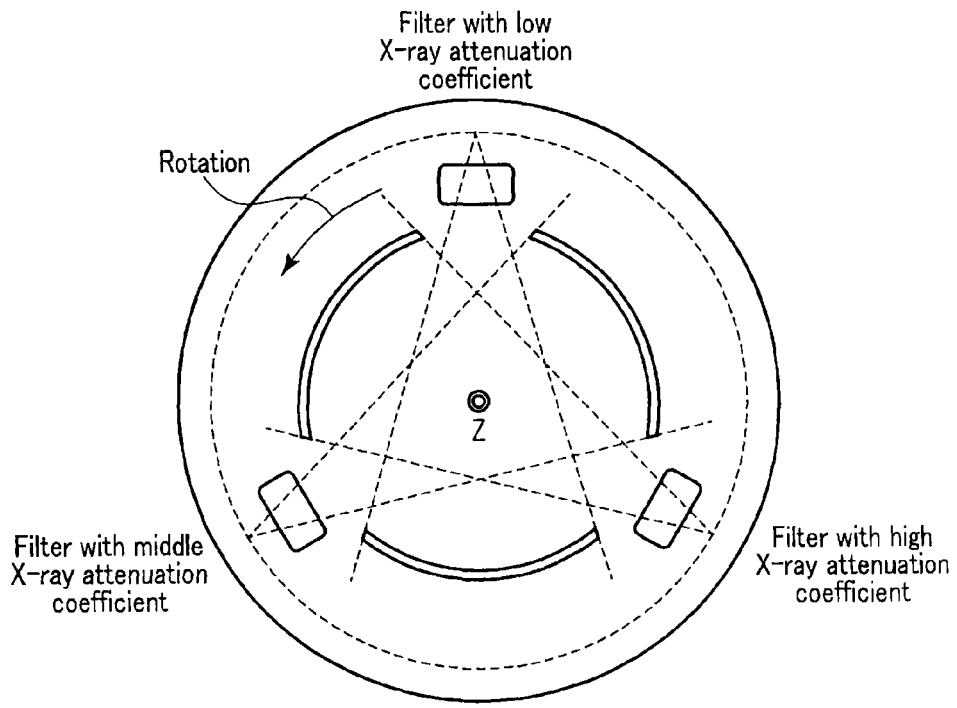
FIG. 17A is a plan view showing the placement of the X-ray sources, the wedge filters, and the post-collimators at time t when the number of X-ray sources simultaneously driven is three in filter-based spectral CT according to the application example of the first embodiment.
Figure 17B:
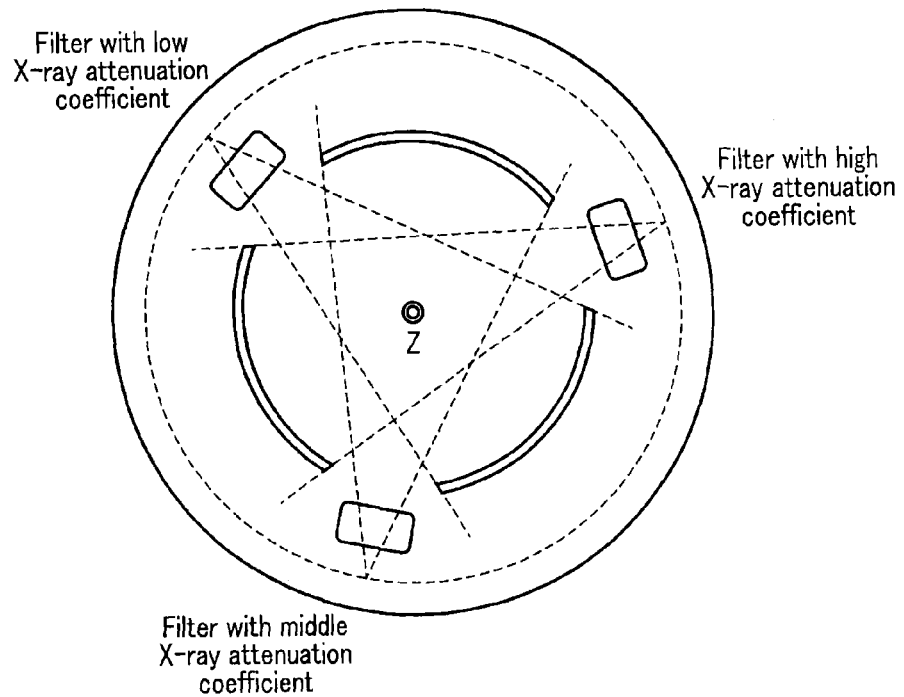
FIG. 17B is a plan view showing the placement of the X-ray sources, the wedge filters, and the post-collimators at time t+Δt when the number of X-ray sources simultaneously driven is three in filter-based spectral CT according to the application example of the first embodiment.

FIGS. 17A and 17B are plan views each showing the placement of the X-ray sources 11, the wedge filters 21, and the post-collimators when the number of directions in which irradiation is simultaneously performed three in filter-based spectral CT. FIG. 17A shows the placement at time t. FIG. 17B shows the placement at time t+Δt. As described above, when the number of directions in which irradiation is simultaneously performed is three, the three wedge filters 21 are held by the filter support member 23 along a circumference at equal intervals, and the three post-collimators 27 are held by the collimator support member 29. The three wedge filters 21 are formed from different materials to make them exhibit different X-ray attenuation effects with respect to X-rays from the three X-ray sources 11. For example, the respective wedge filters 21 are preferably formed from arbitrary metals with different X-ray attenuation coefficients. More specifically, the first, second, and third wedge filters are preferably formed from copper, iodine, and gadolinium, respectively.

As in tube-voltage-based spectral CT, the data collection circuit 37 collects raw data from the respective X-ray detectors 15 for each view. In this case, raw data originating from the X-rays transmitted through the wedge filter 21 with a low X-ray attenuation coefficient is called high-energy raw data, raw data originating from the X-rays transmitted through the wedge filter 21 with a middle X-ray attenuation coefficient is called middle-energy raw data, and raw data originating from the X-rays transmitted through the wedge filter 21 with a high X-ray attenuation coefficient is called low-energy raw data. The reconstruction unit 55 reconstructs a CT image (high-energy CT image) based on the high-energy raw data, a CT image (middle-energy CT image) based on the middle-energy raw data, and a CT image (low-energy CT image) based on the low-energy raw data. A high-energy CT image is substantially equivalent to a high-tube-voltage CT image. A middle-energy CT image is substantially equivalent to a middle-tube-voltage CT image. A low-energy CT image is substantially equivalent to a low-tube-voltage CT image. In addition, the reconstruction unit 55 may generate an image concerning a predetermined base material (a base material image) based on high-energy raw data, middle-energy raw data, and low-energy raw data or may generate a monochromatic X-ray image, a density image, and an effective atomic number image, each based on the base material. The display 69 displays the high-energy CT image, middle-energy CT image, low-energy CT image, base material image, monochromatic X-ray image, density image, and effective atomic number image.

With the above arrangement, the X-ray computed tomography apparatus including the two X-ray source rings 13 and the detector ring 17 implements filter-based spectral CT with respect to each of the two X-ray source rings 13.

Note that in the above description, spectral CT is executed by individually adjusting tube voltages and materials for the wedge filters. However, this embodiment is not limited to this. That is, spectral CT may be executed by optimizing both tube voltages and materials for the wedge filters. In this case, it is preferable to adjust both tube voltages and materials for the wedge filters so as to separate the energy range of X-rays from each X-ray irradiation system constituted by one X-ray source 11, one wedge filter 21, and one post-collimator 27 from the energy range of X-rays from another X-ray irradiation system.

The first embodiment can therefore provide an X-ray computed tomography apparatus which can execute high-speed imaging.

Second Embodiment

A photon counting CT apparatus according to the second embodiment will be described next. Note that in the following description, the same reference numerals denote constituent elements having almost the same functions as those in the first embodiment, and a repetitive description will be made only when required.

Figure 18:
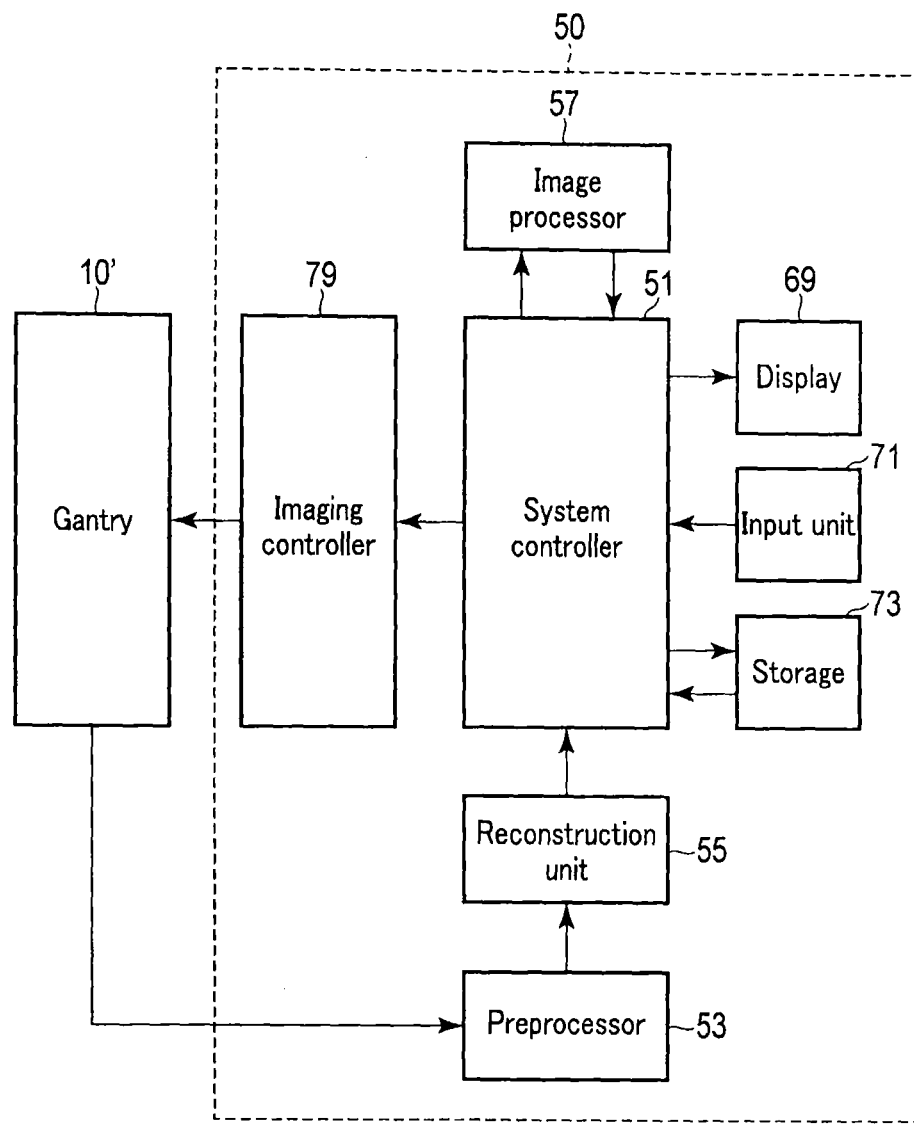
FIG. 18 is a functional block diagram of a photon counting CT apparatus according to the second embodiment.
Figure 19:
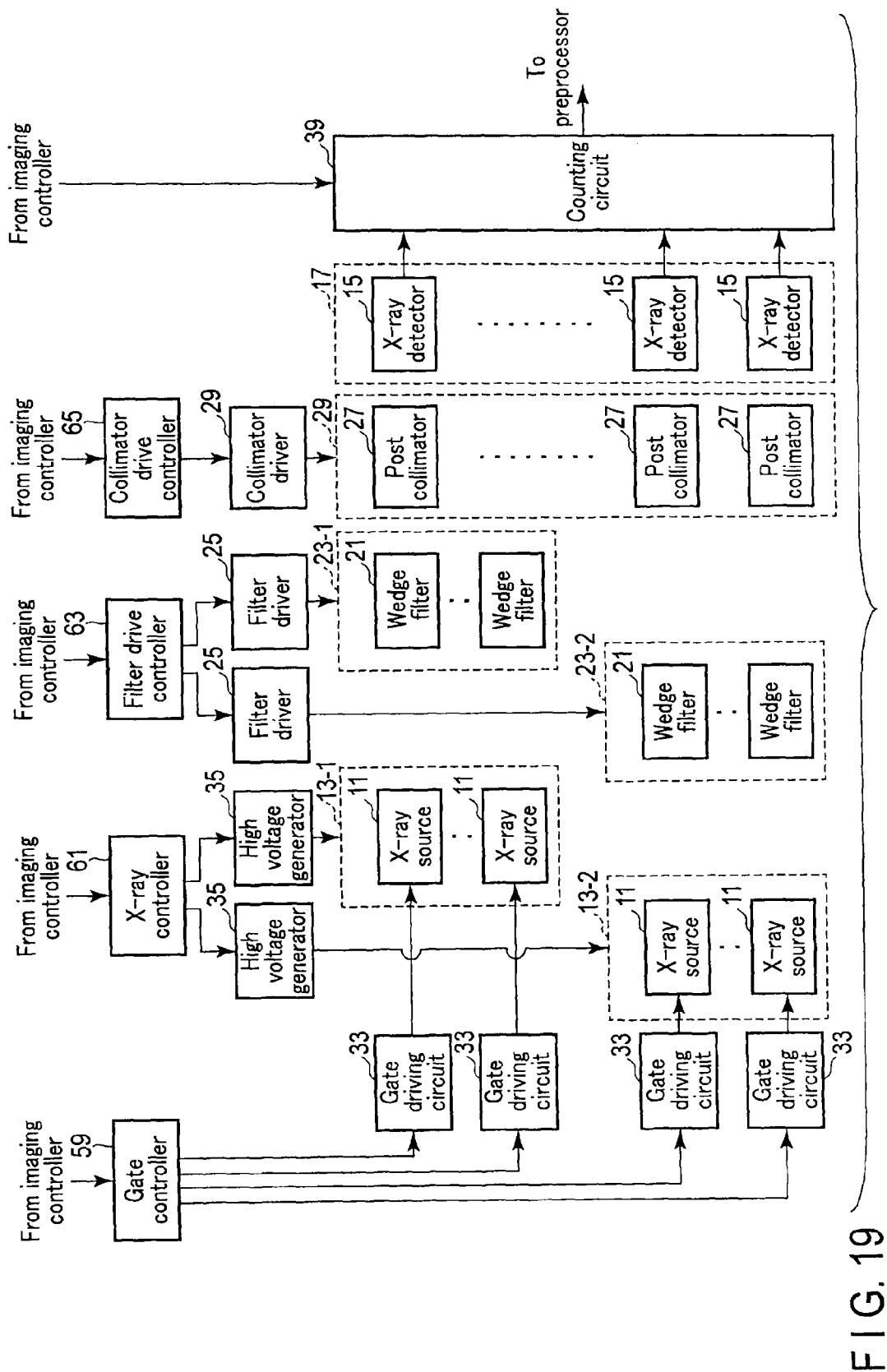
FIG. 19 is a functional block diagram of a gantry in FIG. 15.

FIG. 18 is a functional block diagram of the photon counting CT apparatus according to the second embodiment. As shown in FIG. 18, the photon counting. CT apparatus according to the second embodiment includes a gantry 10' in place of the gantry 10 in the X-ray computed tomography apparatus according to the first embodiment, the preprocessor 53, the reconstruction unit 55, and an imaging controller 79 in place of the imaging controller 67. FIG. 19 is a functional block diagram of the gantry 10' according to the second embodiment. As shown in FIG. 19, the gantry includes a counting circuit 39 in place of the data collection circuit 37 of the X-ray computed tomography apparatus according to the first embodiment.

The counting circuit 39 counts the numbers of X-ray photons detected by X-ray detectors 15 in a plurality of energy bands under the control of the imaging controller 79. As counting schemes used by the counting circuit 39, the sinogram mode scheme and the list mode scheme are known. In the sinogram mode scheme, the counting circuit 39 performs pulse height discrimination of electrical pulses from each X-ray detector 15, and counts the number of electrical pulses in each of preset energy bands as the number of X-ray photons for each X-ray detector 15. The plurality of energy bands have been set via an input unit 71. In the list mode scheme, the counting circuit 39 performs pulse height discrimination of electrical pulses from each X-ray detector 15, and records the pulse height value of each electrical pulse as the energy value of each X-ray photon in association with the detection time. The counting circuit 39 refers to the record to classify X-ray photons into a plurality of predetermined energy bands and count the number of X-ray photons in each of the plurality of energy bands for each view. The count number data are supplied to the preprocessor 53.

The preprocessor 53 preprocesses the count number data for each energy band supplied from the counting circuit 39. For example, preprocessing includes integral processing of the numbers of photons, logarithmic conversion, X-ray intensity correction, and offset correction.

The reconstruction unit 55 generates a photon counting CT image expressing the spatial distribution of CT values concerning a visualization target energy band of a plurality of energy bands by applying an image reconstruction algorithm to the count number data obtained by preprocessing for the visualization target energy band.

The imaging controller 79 synchronously controls a gate controller 59, an X-ray controller 61, a filter drive controller 63, a collimator drive controller 65, and the counting circuit 39. As in the first embodiment, the imaging controller 79 synchronously outputs commands to the gate controller 59 and the X-ray controller 61 to switch an X-ray source 11 as an X-ray generation target in synchronism with the switching of a view. Since the operations of the gate controller 59 and the X-ray controller 61 are the same as those in the first embodiment, a description of them will be omitted. In addition, as in the first embodiment, the imaging controller 79 synchronously outputs commands to the filter drive controller 63 and the collimator drive controller 65 so as to set a wedge filter 21 in front of the X-ray source 11 as an X-ray generation target and set a post-collimator 27 in front of the X-ray detector 15 located on the opposite side of a rotation axis Z to the X-ray source 11. Since the operations of the filter drive controller 63 and the collimator drive controller 65 are the same as those in the first embodiment, a description of them will be omitted. Furthermore, the imaging controller 79 controls the counting circuit 39 so as to read out an electrical signal from the X-ray detector 15 in synchronism with the switching of a view. Since the switching of a view is the same as that in the first embodiment, a description of it will be omitted. In addition, the imaging controller 79 synchronously controls the gate controller 59 and the X-ray controller 61 to cause two X-ray source rings 13 to alternately generate X-ray photons as in the first embodiment.

The second embodiment can therefore provide a photon counting CT apparatus which can execute high-speed imaging. In addition, as compared with the X-ray computed tomography apparatus according to the first embodiment, the photon counting CT apparatus according to the second embodiment can reduce the exposure dose of a subject S by photon counting CT. Furthermore, it is possible to improve the spatial resolution of a photon counting CT image by applying X-rays from the two X-ray source rings 13.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography apparatus comprising:
   two X ray source rings arrayed along a central axis, each of the two X ray source rings including a plurality of X ray sources arrayed on a circumference, and the plurality of X ray sources including a plurality of electron emission sources arrayed on a circumference, a plurality of gate electrodes configured to apply electric fields to the plurality of electron emission sources, and an anode configured to generate X rays upon receiving electrons generated from the plurality of electron emission sources upon application of electric fields by the plurality of gate electrodes;
   a gate electrode driver configured to individually drive the plurality of gate electrodes;
   a controller configured to control the gate electrode driver to cause the plurality of X ray sources of each of the two X ray source rings to generate X rays in accordance with a predetermined order;
   a single detector ring provided between the two X ray source rings and including a plurality of X ray detectors arrayed on a circumference, each of the plurality of X ray detectors detecting X rays from the two X ray source rings;
   a data collection unit configured to collect digital data corresponding to an intensity of the detected X rays; and
   a reconstruction unit configured to reconstruct a CT image based on the digital data,
   wherein the controller controls the gate electrode driver to alternately generate X rays from the two X ray source rings.

2. The X ray computed tomography apparatus of claim 1, wherein the two X ray source rings includes a first X ray source ring and a second X ray source ring, an X ray source as an X ray generation target included in the first X ray source ring and an X ray source as an X ray generation target included in the second X ray source ring are set at substantially the same angle around the central axis.

3. An X ray computed tomography apparatus comprising:
   two X ray source rings arrayed along a central axis, each of the two X ray source rings including a plurality of X ray sources arrayed on a circumference, and the plurality of X ray sources including a plurality of electron emission sources arrayed on a circumference, a plurality of gate electrodes configured to apply electric fields to the plurality of electron emission sources, and an anode configured to generate X rays upon receiving electrons generated from the plurality of electron emission sources upon application of electric fields by the plurality of gate electrodes;
   a gate electrode driver configured to individually drive the plurality of gate electrodes;
   a controller configured to control the gate electrode driver to cause the plurality of X ray sources of each of the two X ray source rings to generate X rays in accordance with a predetermined order;
   a single detector ring provided between the two X ray source rings and including a plurality of X ray detectors arrayed on a circumference, each of the plurality of X ray detectors detecting X rays from the two X ray source rings;
   a data collection unit configured to collect digital data corresponding to an intensity of the detected X rays; and
   a reconstruction unit configured to reconstruct a CT image based on the digital data,
   wherein the controller controls the gate electrode driver to simultaneously generate X rays from the two X ray source rings.

4. The X ray computed tomography apparatus of claim 3, wherein the two X ray source rings includes a first X ray source ring and a second X ray source ring, the controller sets a difference in angle around the central axis between an X ray source as an X ray generation target included in the first X ray source ring and an X ray source as an X ray generation target included in the second X ray source ring to not less than 90°.

5. An X ray computed tomography apparatus comprising:
   two X ray source rings arrayed along a central axis, each of the two X ray source rings including a plurality of X ray sources arrayed on a circumference, and the plurality of X ray sources including a plurality of electron emission sources arrayed on a circumference, a plurality of gate electrodes configured to apply electric fields to the plurality of electron emission sources, and an anode configured to generate X rays upon receiving electrons generated from the plurality of electron emission sources upon application of electric fields by the plurality of gate electrodes;
   a gate electrode driver configured to individually drive the plurality of gate electrodes;
   a single detector ring provided between the two X ray source rings and including a plurality of X ray detectors arrayed on a circumference, each of the plurality of X ray detectors detecting X rays from the two X ray source rings;
   two filter support mechanisms provided on the two X ray source rings;
   a plurality of wedge filters rotatably supported on each of the two filter support mechanisms;
   a support mechanism driver configured to drive the two filter support mechanisms;
   a controller configured to control the gate electrode driver and the support mechanism driver to cause the plurality of X ray sources of each of the two X ray source rings to generate X rays in accordance with a predetermined order and to rotate the plurality of wedge filters in synchronism with generation of X rays from the X ray source;
   a data collection unit configured to collect digital data corresponding to an intensity of the detected X rays; and
   a reconstruction unit configured to reconstruct a CT image based on the digital data, wherein
   a plurality of wedge filters provided on each of the two filter support mechanism are formed from materials having different X ray attenuation coefficients, and
   two wedge filters provided on the two filter support mechanisms and located at the same angle around the central axis are formed from materials having the same X ray attenuation coefficient.

6. An X ray computed tomography apparatus comprising:
   two X ray source rings arrayed along a central axis, each of the two X ray source rings including a plurality of X ray sources arrayed on a circumference, and the plurality of X ray sources including a plurality of electron emission sources arrayed on a circumference, a plurality of gate electrodes configured to apply electric fields to the plurality of electron emission sources, and an anode configured to generate X rays upon receiving electrons generated from the plurality of electron emission sources upon application of electric fields by the plurality of gate electrodes;

a gate electrode driver configured to individually drive the plurality of gate electrodes;

a single detector ring provided between the two X ray source rings and including a plurality of X ray detectors arrayed on a circumference, each of the plurality of X ray detectors detecting X rays from the two X ray source rings;

a plurality of post collimators provided on the X ray detection ring and arrayed circumferentially;

a collimator support mechanism configured to support the plurality of post collimators rotatable about the central axis;

a support mechanism driver configured to drive the collimator support mechanism;

a controller configured to control the gate electrode driver and the support mechanism driver to cause the plurality of X ray sources of each of the two X ray source rings to generate X rays in accordance with a predetermined order and to rotate the plurality of post collimators in synchronism with generation of X rays from the X ray source;

a data collection unit configured to collect digital data corresponding to an intensity of the detected X rays; and a reconstruction unit configured to reconstruct a CT image based on the digital data, wherein the plurality of post collimators are formed from materials having different X ray attenuation coefficients.

* * * * *